United States Patent
Flygare et al.

(10) Patent No.: US 6,962,929 B2
(45) Date of Patent: Nov. 8, 2005

(54) PENTAFLUOROBENZENESULFONAMIDES AND ANALOGS

(75) Inventors: John A. Flygare, Burlingame, CA (US); Julio Cesar Medina, San Carlos, CA (US); Bei Shan, Redwood City, CA (US); David Louis Clark, Albany, CA (US); Terry J. Rosen, Burlingame, CA (US)

(73) Assignee: Tularik Inc., South San Francisco, CA (US)

(*) Notice: Subject to any disclaimer, the term of this patent is extended or adjusted under 35 U.S.C. 154(b) by 0 days.

(21) Appl. No.: 10/270,259

(22) Filed: Oct. 11, 2002

(65) Prior Publication Data

US 2003/0162817 A1 Aug. 28, 2003

Related U.S. Application Data

(63) Continuation of application No. 08/896,280, filed on Jul. 18, 1997, now Pat. No. 6,482,860.
(60) Provisional application No. 60/022,198, filed on Jul. 19, 1996.

(51) Int. Cl.[7] .................. A61K 31/47; A61K 31/44; A61K 31/415; A61K 31/38; A61K 31/34
(52) U.S. Cl. .............. 514/312; 514/352; 514/353; 514/357; 514/406; 514/412; 514/443; 514/447; 514/469; 514/604; 546/153; 546/307; 546/312; 548/362.5; 548/469; 548/509; 549/57; 549/68; 549/404; 564/91; 564/92
(58) Field of Search .................. 514/312, 352, 514/353, 357, 406, 412, 443, 447, 469; 546/153, 307, 312; 548/362.5, 469, 509; 549/57, 68, 404

(56) References Cited

U.S. PATENT DOCUMENTS

| | | | |
|---|---|---|---|
| 1,955,207 A | 4/1934 | Stotter et al. ........... 167/37 |
| 2,402,623 A | 6/1946 | Hester et al. ........... 260/558 |
| 3,034,955 A | 5/1962 | Frick et al. ........... 167/37 |
| 4,443,477 A | 4/1984 | Witte et al. |
| 4,881,969 A | 11/1989 | Saupe et al. ........... 71/94 |
| 4,883,914 A | 11/1989 | Alvarado et al. ........... 564/91 |
| 4,900,867 A | 2/1990 | Wilkes et al. ........... 564/91 |
| 5,093,340 A | 3/1992 | Mohrs et al. |
| 5,250,549 A | 10/1993 | Yoshino et al. ........... 514/345 |
| 5,385,931 A | 1/1995 | Bigg et al. ........... 514/443 |
| 5,387,709 A | 2/1995 | Lardy et al. ........... 558/388 |
| 5,591,503 A | 1/1997 | Pews et al. |
| 5,610,320 A | 3/1997 | Yoshino et al. |
| 5,773,236 A | 6/1998 | Diwu et al. |
| 5,880,151 A | 3/1999 | Medina et al. ........... 514/518 |
| 5,891,917 A * | 4/1999 | Tang et al. ........... 514/604 |
| 6,121,304 A | 9/2000 | Flygare et al. |
| 6,153,585 A | 11/2000 | Rubenstein et al. |
| 6,284,923 B1 | 9/2001 | Medina et al. |
| 6,316,484 B1 | 11/2001 | Flygare et al. |
| 6,355,628 B1 | 3/2002 | Schwendner et al. |
| 6,388,131 B2 | 5/2002 | Medina et al. |
| 6,482,860 B1 | 11/2002 | Flygare et al. |
| 6,521,658 B1 * | 2/2003 | Li et al. ........... 514/415 |
| 6,630,513 B1 | 10/2003 | Rubenstein et al. |
| 2002/0143036 A1 | 10/2002 | Flygare et al. |
| 2002/0177548 A1 | 11/2002 | Schwendner et al. |

FOREIGN PATENT DOCUMENTS

| | | |
|---|---|---|
| DE | 3623184 A | 2/1992 |
| EP | 0391799 A | 10/1990 |
| EP | 91307061.1 | 1/1991 |
| EP | 0 469 901 A1 | 2/1992 |
| EP | 472 449 A2 | 2/1992 |
| EP | 0472499 A | 2/1992 |
| EP | WO 97/30677 | 4/1994 |
| GB | 1242057 | 8/1971 |
| GB | 1306564 | 2/1973 |
| WO | WO 99/24407 A1 | 5/1999 |

OTHER PUBLICATIONS

U.S. Appl. No. 08/605,431, filed Feb. 22, 1996, Flygare et al.

March, J., *Advanced Organic Chemistry*, 4th Edition, John Wiley & Sons, p. 497 (1992).

Yoshimoto, M., et al., "Correlation analysis of Baker's studies on enzyme inhibition, 2. Chymotrypsin, trypsin, thymidine phosphorylase, uridine phosphorylase, thymidylate synthetase, cylosine nucleoside deaminase, dihydrofolate reductase, malate dehydrogenase, glutamate dehydrogenase, lactate dehydrogenase, and glyceraldehydes–phosphate dehydrogenase" J. Med. Chem. 19(1):71–98 (1976).

(Continued)

*Primary Examiner*—Peter O'Sullivan
(74) *Attorney, Agent, or Firm*—Townsend and Townsend and Crew LLP

(57) ABSTRACT

The invention provides methods and compositions relating to novel pentafluorophenylsulfonamide derivatives and analogs and their use as pharmacologically active agents. The compositions find particular use as pharmacological agents in the treatment of disease states, particularly cancer, vascular restenosis, microbial infections, and psoriasis, or as lead compounds for the development of such agents. The compositions include compounds of the general formula I:

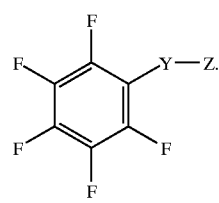

20 Claims, No Drawings

OTHER PUBLICATIONS

Ishii et al., "Silver halide color photographic material containing magenta coupler" CAPLUS Abstract 108:177077 (1988).

Iwata et al., "Preparation of thiazolidine derivatives as platelet–activating factor antagonists" CAPLUS Abstract 116:214490 (1992).

Nazareth et al., "Electrophore–labeling and alkylation of standards of nucleic acid pyrimidine bases for analysis by gas chromatography with electron–capture detection" CAPLUS Abstract 102:109290 (1985).

Posner et al., "Diels–alder cycloadditions using electrophilic sulfonyl pyridones" CAPLUS Abstract 107:23211 (1987).

Fielding, et al.; "Synthesis and reactions of 4–sulpho–2,3,5,6,–tetrafluorobenzoic acid", *Journal of Fluorine Chemistry*, Oct. 1992, vol. 59, No. 1, pp. 15–31.

Raibekas, et al.; "Affinity Probing of Flavin Binding Sites. 2. Identification of a Reactive Cysteine in the Flavin Domain of *Escherichia coli* DNA Photolyase"; *Biochemistry* 1994, vol. 33, No. 42, pp. 12656–12664.

Shealy, et al.; "2–Haloethylating Agents for Cancer Chemotherapy. 2–Haloethyl Sulfonates"; *Journal of Medicinal Chemistry*, Aug. 1983, vol. 26, No. 8, pp. 1168–1173.

Olander, et al.; "A Study of the Binding of Two Sulfonamides to Carbonic Anhydrase"; *Journal of the American Chemical Society*, Mar. 1973, vol. 95, No. 5, pp. 1616–1621.

Hawkinson, et al.; "Studies of the Solvolysis of 2–Adamantyl Pentafluorobenzenesulfonate: A $Y_{pfbs}$ Scale [1]"; *The Journal of Organic Chemistry*, Aug., 1988, vol. 53, No. 16, pp. 3857–3860.

Bai, et al.; "Identification of the Cysteine Residue of β–Tubulin Alkylated by the Antimitotic Agent 2,4–Dichlorobenzyl Thiocyanate, Facilitated by Separation of the Protein Subunits of Tubulin by Hydrophobic Column Chromatography"; *Biochemistry* 1989, vol. 28, pp. 5606–5612.

Fadeeva, V.P., et al., "Gas–chromatographic separation of sulfur–and fluorine–containing pyrolysis products", *Chemical Abstracts*, 76:(5) (Jan. 31, 1972).

Gerig et al., "Aromatic Ring Dynamics in a Carbonic Anhydrase–Inhibitor Complex", *Journal of the Chemical Society Chemical Communications*, No. 6, pp 482–484 (1987).

Luduena, E.F., et al. Interaction of Ethacrynic Acid with Bovine Brain Tubulin, *Biochemical Pharmacology*, 47:(9) 1677–1681 (Apr. 29, 1994).

* cited by examiner

PENTAFLUOROBENZENESULFONAMIDES AND ANALOGS

CROSS-REFERENCE TO RELATED APPLICATIONS

This application is a continuation of U.S. application Ser. No. 08/896,280, filed Jul. 18, 1997 now U.S. Pat. No. 6,482,860, and claims benefit of U.S. Provisional Application No. 60/022,198, filed Jul. 19, 1996, the contents of which are incorporated herein by reference.

FIELD OF THE INVENTION

The field of the invention is pentafluorobenzenesulfonamide derivatives and analogs and their use as pharmacologically active agents.

BACKGROUND

A number of human diseases stem from processes of uncontrolled or abnormal cellular proliferation. Most prevalent among these is cancer, a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disruptors (e.g., vincristine, vinblastine, paclitaxel), DNA intercalators (e.g., doxorubicin, daunomycin, cisplatin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells even after prolonged exposure to the drug. Unfortunately, none of the current chemotherapies possess an ideal profile. Most possess very narrow therapeutic indexes, and in practically every instance cancerous cells exposed to slightly sublethal concentrations of a chemotherapeutic agent will develop resistance to such an agent, and quite often cross-resistance to several other antineoplastic agents.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

Accordingly, it is one object of the present invention to provide compounds which directly or indirectly are toxic to actively dividing cells and are useful in the treatment of cancer, viral and bacterial infections, vascular restenosis, inflammatory diseases, autoimmune diseases, and psoriasis.

A further object of the present invention is to provide therapeutic compositions for treating said conditions.

Still further objects are to provide methods for killing actively proliferating cells, such as cancerous, bacterial, or epithelial cells, and treating all types of cancers, infections, inflammatory, and generally proliferative conditions. A further object is to provide methods for treating other medical conditions characterized by the presence of rapidly proliferating cells, such as psoriasis and other skin disorders.

Other objects, features and advantages will become apparent to those skilled in the art from the following description and claims.

SUMMARY OF THE INVENTION

The invention provides methods and compositions relating to novel pentafluorophenylsulfonamide derivatives and analogs and their use as pharmacologically active agents. The compositions find particular use as pharmacological agents in the treatment of disease states, particularly cancer, bacterial infections and psoriasis, or as lead compounds for the development of such agents.

In one embodiment, the invention provides for the pharmaceutical use of compounds of the general formula I and for pharmaceutically acceptable compositions of compounds of formula I:

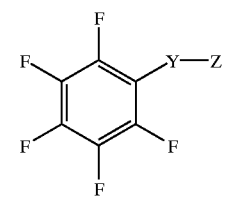

or a physiologically acceptable salt thereof, wherein:
Y is —S(O)— or —S(O)$_2$—;
Z is —NR$^1$R$^2$ or —OR$^3$, where R$^1$ and R$^2$ are independently selected from hydrogen,
substituted or unsubstituted (C1–C10)alkyl,
substituted or unsubstituted (C1–C10)alkoxy,
substituted or unsubstituted (C3–C6)alkenyl,
substituted or unsubstituted (C2–C6)heteroalkyl,
substituted or unsubstituted (C3–C6)heteroalkenyl,
substituted or unsubstituted (C3–C6)alkynyl,
substituted or unsubstituted (C3–C8)cycloalkyl,
substituted or unsubstituted (C5–C7)cycloalkenyl,
substituted or unsubstituted (C5–C7)cycloalkadienyl,
substituted or unsubstituted aryl,
substituted or unsubstituted aryloxy,
substituted or unsubstituted aryl-(C3–C8)cycloalkyl,
substituted or unsubstituted aryl-(C5–C7)cycloalkenyl,
substituted or unsubstituted aryloxy-(C3–C8)cycloalkyl, substituted or unsubstituted aryl-(C1–C4)alkyl,
substituted or unsubstituted aryl-(C1–C4)alkoxy,
substituted or unsubstituted aryl-(C1–C4)heteroalkyl,
substituted or unsubstituted aryl-(C3–C6)alkenyl,
substituted or unsubstituted aryloxy-(C1–C4)alkyl,
substituted or unsubstituted aryloxy-(C2–C4)heteroalkyl,
substituted or unsubstituted heteroaryl,
substituted or unsubstituted heteroaryloxy,
substituted or unsubstituted heteroaryl-(C1–C4)alkyl,
substituted or unsubstituted heteroaryl-(C1–C4)alkoxy,
substituted or unsubstituted heteroaryl-(C1–C4)heteroalkyl,
substituted or unsubstituted heteroaryl-(C3–C6)alkenyl,
substituted or unsubstituted heteroaryloxy-(C1–C4)alkyl, and
substituted or unsubstituted heteroaryloxy-(C2–C4) heteroalkyl,
wherein $R^1$ and $R^2$ may be connected by a linking group E to give a substituent of the formula

wherein E represents a bond, (C1–C4) alkylene, or (C1–C4) heteroalkylene, and the ring formed by $R^1$, E, $R^2$ and the nitrogen contains no more than 8 atoms, or preferably the $R^1$ and $R^2$ may be covalently joined in a moiety that forms a 5- or 6-membered heterocyclic ring with the nitrogen atom of $NR^1R^2$;
and where $R^3$ is a substituted or unsubstituted aryl or heteroaryl group.

Substituents for the alkyl, alkoxy, alkenyl, heteroalkyl, heteroalkenyl, alkynyl, cycloalkyl, heterocycloalkyl, cycloalkenyl, and cycloalkadienyl radicals are selected independently from
—H
—OH
—O—(C1–C10)alkyl
=O
—$NH_2$
—NH—(C1–C10)alkyl
—N[(C1–C10)alkyl]$_2$
—SH
—S—(C1–C10)alkyl
-halo
—Si[(C1–C10)alkyl]$_3$
in a number ranging from zero to (2N+1), where N is the total number of carbon atoms in such radical.

Substituents for the aryl and heteroaryl groups are selected independently from
-halo
—OH
—O—R'
—O—C(O)—R'
—$NH_2$
—NHR'
—NR'R"
—SH
—SR'
—R'
—CN
—$NO_2$
—$CO_2H$
—$CO_2$—R'
—$CONH_2$
—CONH—R'
—CONR'R"
—O—C(O)—NH—R'
—O—C(O)—NR'R"
—NH—C(O)—R'
—NR"—C(O)—R'
—NH—C(O)—OR'
—NR"—C(O)—R'
—NH—C($NH_2$)=NH
—NR'—C($NH_2$)=NH
—NH—C($NH_2$)=NR'
—S(O)—R'
—S(O)$_2$—R'
—S(O)$_2$—NH—R'
—S(O)$_2$—NR'R"
—$N_3$
—CH(Ph)$_2$
substituted or unsubstituted aryloxy
substituted or unsubstituted arylamino
substituted or unsubstituted heteroarylamino
substituted or unsubstituted heteroaryloxy
substituted or unsubstituted aryl-(C1–C4)alkoxy,
substituted or unsubstituted heteroaryl-(C1–C4)alkoxy,
perfluoro(C1–C4)alkoxy, and
perfluoro(C1–C4)alkyl,
in a number ranging from zero to the total number of open valences on the aromatic ring system;
and where R' and R" are independently selected from:
substituted or unsubstituted (C1–C10)alkyl,
substituted or unsubstituted (C1–C10)heteroalkyl,
substituted or unsubstituted (C2–C6)alkenyl,
substituted or unsubstituted (C2–C6)heteroalkenyl,
substituted or unsubstituted (C2–C6)alkynyl,
substituted or unsubstituted (C3–C8)cycloalkyl,
substituted or unsubstituted (C3–C8)heterocycloalkyl,
substituted or unsubstituted (C5–C6)cycloalkenyl,
substituted or unsubstituted (C5–C6)cycloalkadienyl,
substituted or unsubstituted aryl,
substituted or unsubstituted aryl-(C1–C4)alkyl,
substituted or unsubstituted aryl-(C1–C4)heteroalkyl,
substituted or unsubstituted aryl-(C2–C6)alkenyl,
substituted or unsubstituted aryloxy-(C1–C4)alkyl,
substituted or unsubstituted aryloxy-(C1–C4)heteroalkyl,
substituted or unsubstituted heteroaryl,
substituted or unsubstituted heteroaryl-(C1–C4)alkyl,
substituted or unsubstituted heteroaryl-(C1–C4)heteroalkyl,
substituted or unsubstituted heteroaryl-(C2–C6)alkenyl,
substituted or unsubstituted heteroaryloxy-(C1–C4)alkyl, and
substituted or unsubstituted heteroaryloxy-(C1–C4) heteroalkyl.

Two of the substituents on adjacent atoms of the aryl or heteroaryl ring may optionally be replaced with a substituent of the formula —T—C(O)—($CH_2$)$_n$—U—, wherein T and U are independently selected from N, O, and C, and n=0–2. Alternatively, two of the substituents on adjacent atoms of the aryl or heteroaryl ring may optionally be replaced with a substituent of the formula —A—(CH2)p-B—, wherein A and B are independently selected from C, O, N, S, SO, $SO_2$, and $SO_2NR'$, and p=1–3. One of the single bonds of the new ring so formed may optionally be replaced with a double bond. Alternatively, two of the substituents on adjacent atoms of the aryl or heteroaryl ring may optionally be replaced with a substituent of the formula —($CH_2$)$_q$—X—($CH_2$)$_r$—, where q and r are independently 1–3, and X is selected from O, N, S, SO, $SO_2$ and $SO_2NR'$. The substituent R' in $SO_2NR'$ is selected from hydrogen or (C1–C6)alkyl.

In another embodiment, the invention provides novel methods for the use of pharmaceutical compositions containing compounds of the foregoing description of the general formula I. The invention provides novel methods for treating pathology such as cancer, bacterial infections and psoriasis, including administering to a patient an effective formulation of one or more of the subject compositions.

In another embodiment, the invention provides chemically-stable, pharmacologically active compounds of general formula I:

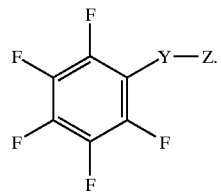

I or a pharmaceutically acceptable salt thereof, wherein:
Y is —S(O)— or —S(O$_2$)—; and
Z is NR$^1$R$^2$, wherein R$^2$ is an optionally substituted aryl or heteroaryl group, and R$^1$ is selected from:
hydrogen,
substituted or unsubstituted (C1–C10)alkyl,
substituted or unsubstituted (C1–C10)alkoxy,
substituted or unsubstituted (C3–C6)alkenyl,
substituted or unsubstituted (C2–C6)heteroalkyl,
substituted or unsubstituted (C3–C6)heteroalkenyl,
substituted or unsubstituted (C3–C6)alkynyl,
substituted or unsubstituted (C3–C8)cycloalkyl,
substituted or unsubstituted (C5–C7)cycloalkenyl,
substituted or unsubstituted (C5–C7)cycloalkadienyl,
substituted or unsubstituted aryl,
substituted or unsubstituted aryloxy,
substituted or unsubstituted aryl-(C3–C8)cycloalkyl,
substituted or unsubstituted aryl-(C5–C7)cycloalkenyl,
substituted or unsubstituted aryloxy-(C3–C8)cycloalkyl,
substituted or unsubstituted aryl-(C1–C4)alkyl,
substituted or unsubstituted aryl-(C1–C4)alkoxy,
substituted or unsubstituted aryl-(C1–C4)heteroalkyl,
substituted or unsubstituted aryl-(C3–C6)alkenyl,
substituted or unsubstituted aryloxy-(C1–C4)alkyl,
substituted or unsubstituted aryloxy-(C2–C4)heteroalkyl,
substituted or unsubstituted heteroaryl,
substituted or unsubstituted heteroaryloxy,
substituted or unsubstituted heteroaryl-(C1–C4)alkyl,
substituted or unsubstituted heteroaryl-(C1–C4)alkoxy,
substituted or unsubstituted heteroaryl-(C1–C4)heteroalkyl,
substituted or unsubstituted heteroaryl-(C3–C6)alkenyl,
substituted or unsubstituted heteroaryloxy-(C1–C4)alkyl, and
substituted or unsubstituted heteroaryloxy-(C2–C4) heteroalkyl,
wherein R$^1$ and R$^2$ may be connected by a linking group E to give a substituent of the formula

wherein E represents a bond, (C1–C4) alkylene, or (C1–C4) heteroalkylene, and the ring formed by R$^1$, E, R$^2$ and the nitrogen contains no more than 8 atoms, or preferably the R$^1$ and R$^2$ may be covalently joined in a moiety that forms a 5- or 6-membered heterocyclic ring with the nitrogen atom of NR$^1$R$^2$;

provided that:
in the case that Y is —S(O$_2$)—, and R$^1$ is hydrogen or methyl, then R$^2$ is substituted phenyl or heteroaryl group;
in the case that Y is —S(O$_2$)— and R$^2$ is a ring system chosen from 1-naphthyl, 5-quinolyl, or 4-pyridyl, then either R$^1$ is not hydrogen or R$^2$ is substituted by at least one substituent that is not hydrogen;
in the case that Y is —S(O$_2$)—, R$^2$ is phenyl, and R$^1$ is a propylene unit attaching the nitrogen of —NR$^1$R$^2$— to the 2- position of the phenyl ring in relation to the sulfonamido group to form a 1,2,3,4-tetrahydroquinoline system, one or more of the remaining valences on the bicyclic system so formed is substituted with at least one substituent that is not hydrogen;
in the case that Y is —S(O$_2$)— and R$^2$ is phenyl substituted with 3-(1-hydroxyethyl), 3-dimethylamino, 4-dimethylamino, 4-phenyl, 3-hydroxy, 3-hydroxy-4-diethylaminomethyl, 3,4-methylenedioxy, 3,4-ethylenedioxy, 2-(1-pyrrolyl), or 2-methoxy-4-(1-morpholino), then either R$^1$ is not hydrogen or when R$^1$ is hydrogen, one or more of the remaining valences on the phenyl ring of R$^2$ is substituted with a substituent that is not hydrogen;
in the case that Y is —S(O$_2$)— and R$^2$ is 2-methylbenzothiazol-5-yl, 6-hydroxy-4-methyl-pyrimidin-2-yl, 3-carbomethoxypyrazin-2-yl, 5-carbomethoxypyrazin-2-yl, 4-carboethoxy-1-phenylpyrazol-5-yl, 3-methylpyrazol-5-yl, 4-chloro-2-methylthiopyrimidin-6-yl, 2-trifluoromethyl-1,3,4-thiadiazol-5-yl, 5,6,7,8-tetrahydro-2-naphthyl, 4-methylthiazol-2-yl, 6,7-dihydroindan-5-yl, 7-chloro-5-methyl-1,8-naphthyridin-2-yl, 5,7-dimethyl-1,8-naphthyridin-2-yl, or 3-cyanopyrazol-4-yl, R$^1$ is a group other than hydrogen.

DETAILED DESCRIPTION OF THE INVENTION

The term "alkyl" by itself or as part of another substituent means, unless otherwise stated, a straight or branched chain hydrocarbon radical, including di- and multi-radicals, having the number of carbon atoms designated (i.e. C1–C10 means one to ten carbons) and includes straight or branched chain groups such as methyl, ethyl, n-propyl, isopropyl, n-butyl, t-butyl, isobutyl, sec-butyl, homologs and isomers of n-pentyl, n-hexyl, 2-methylpentyl, 1,5-dimethylhexyl, 1-methyl-4-isopropylhexyl and the like. The term "alkylene" by itself or as part of another substituent means a divalent radical derived from an alkane, as exemplified by —CH$_2$CH$_2$CH$_2$CH$_2$—. A "lower alkyl" is a shorter chain alkyl, generally having six or fewer carbon atoms.

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. The heteroatom(s) may be placed at any position of the heteroalkyl group, including between the rest of the heteroalkyl group and the fragment to which it is attached, as well as attached to the most distal carbon atom in the heteroalkyl group. Examples include —O—CH$_2$—CH$_2$—CH$_3$, —CH$_2$—CH$_2$—O—CH$_3$, —CH$_2$—CH$_2$—CH$_2$—OH, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —O—CH$_2$—CH$_2$—CH$_2$—NH—CH$_3$, and —CH$_2$—CH$_2$—S(O)$_2$—CH$_3$. Up to two heteroatoms may be consecutive, such as, for example, —CH$_2$—NH—OCH$_3$. The term "heteroalkylene" by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$NH—.

The terms "cycloalkyl" and "heterocycloalkyl", by themselves or in combination with other terms, represent, unless otherwise stated, cyclic versions of "alkyl" and "heteroalkyl", respectively. Examples of cycloalkyl include cyclopentyl, cyclohexyl, cycloheptyl, and the like. Examples of heterocycloalkyl include 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "alkenyl" employed alone or in combination with other terms, means, unless otherwise stated, a stable straight chain or branched monounsaturated or diunsaturated hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A divalent radical derived from an alkene is exemplified by —CH=CH—$CH_2$—.

The term "heteroalkenyl" by itself or in combination with another term means, unless otherwise stated, a stable straight or branched chain monounsaturated or diunsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—O$CH_3$, —CH=CH—N($CH_3$)—$CH_3$, and —$CH_2$—CH=CH—$CH_2$—SH.

The term "alkynyl" employed alone or in combination with other terms, means, unless otherwise stated, a stable straight chain or branched hydrocarbon group having the stated number of carbon atoms, and containing one or two carbon-carbon triple bonds, such as ethynyl, 1- and 3-propynyl, 4-but-1-ynyl, and the higher homologs and isomers.

The term "alkoxy" employed alone or in combination with other terms, means, unless otherwise stated, an alkyl group, as defined above, connected to the rest of the molecule via an oxygen atom, such as, for example, methoxy, ethoxy, 1-propoxy, 2-propoxy and the higher homologs and isomers.

The terms "halo" or "halogen" by themselves or as part of another substituent mean, unless otherwise stated, a fluorine, chlorine, bromine, or iodine atom.

The term "aryl" employed alone or in combination with other terms, means, unless otherwise stated, a phenyl, 1-naphthyl, or 2-naphthyl group. The maximal number of substituents allowed on each one of these ring systems is five, seven, and seven, respectively. Substituents are selected from the group of acceptable substituents listed above.

The term "heteroaryl" by itself or as part of another substituent means, unless otherwise stated, an unsubstituted or substituted, stable, mono- or bicyclic heterocyclic aromatic ring system which consists of carbon atoms and from one to four heteroatoms selected from the group consisting of N, O, and S, and wherein the nitrogen and sulfur heteroatoms may optionally be oxidized, and the nitrogen atom may optionally be quaternized. The heterocyclic system may be attached, unless otherwise stated at any heteroatom or carbon atom which affords a stable structure. The heterocyclic system may be substituted or unsubstituted with one to four substituents independently selected from the list of acceptable aromatic substituents listed above. Examples of such heterocycles include 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Pharmaceutically acceptable salts of the compounds of Formula I include salts of these compounds with relatively nontoxic acids or bases, depending on the particular substituents found on specific compounds of Formula I. When compounds of Formula I contain relatively acidic functionalities, base addition salts can be obtained by contacting the neutral form of compound I with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of Formula I contain relatively basic functionalities, acid addition salts can be obtained by contacting the neutral form of compound I with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like gluconic or galactunoric acids and the like (see, for example, Berge, S. M., et al, "Pharmaceutical Salts", *Journal of Pharmaceutical Science*, Vol. 66, pages 1–19 (1977)). Certain specific compounds of Formula I contain both basic and acidic functionalities that allow the compounds to be converted into either base or acid addition salts.

The free base form may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention possess asymmetric carbon atoms (optical centers); the racemates, diastereomers, and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H) or carbon-14 ($^{14}$C). All isotopic variations of the compounds of the present invention, whether radioactive or not, are intended to be encompassed within the scope of the present invention.

In various preferred embodiments of the pharmaceutical compositions of compounds of formula I, Y is S(O$_2$) and Z is NR$^1$R$^2$, wherein R$^1$ is hydrogen or methyl, and R$^2$ is a substituted phenyl, preferably mono-, di-, or trisubstituted as follows. In one group of preferred compounds, Y is S(O$_2$) and Z is NR$^1$R$^2$, wherein R$^1$ is hydrogen or methyl, and R$^2$ is a phenyl group, preferably substituted in the para position by one of the following groups: hydroxy, amino, (C1–C10)alkoxy, (C1–C10)alkyl, (C1–C10)alkylamino, and [di(C1–C10)alkyl]amino, with up to four additional substituents independently chosen from hydrogen, halogen, (C1–C10)alkoxy, (C1–C10)alkyl, and [di(C1–C10)alkyl]amino. Also preferred are compounds of formula I where there is no linking group E between R$^1$ and R$^2$.

Illustrative examples of pharmaceutical compositions and compounds of the subject pharmaceutical methods include:
2-Fluoro-1-methoxy-4-pentafluorophenylsulfinamidobenzene;
4-Dimethylamino-1-pentafluorophenylsulfinamidobenzene;
4-Methyl-6-methoxy-2-pentafluorophenylsulfonamidopyrimidine;
4,6-Dimethoxy-2-pentafluorophenylsulfonamidopyrimidine;
2-Pentafluorophenylsulfonamidothiophene;
3-Pentafluorophenylsulfonamidothiophene;
3-Pentafluorophenylsulfonamidopyridine;
4-Pentafluorophenylsulfonamidopyridine;
4-(N,N,-Dimethylamino)-1-(N-ethylpentafluorophenylsulfonamido)-benzene;
4-tert-Butoxy-1-pentafluorophenylsulfonamidobenzene;
3-tert-Butoxy-1-pentafluorophenylsulfonamidobenzene;
2-tert-Butoxy-1-pentafluorophenylsulfonamidobenzene;
4-Isopropoxy-1-pentafluorophenylsulfonamidobenzene;
3-Isopropoxy-1-pentafluorophenylsulfonamidobenzene;
2-Isopropoxy-1-pentafluorophenylsulfonamidobenzene;
2-Methoxy-1,3-difluoro-5-pentafluorophenylsulfonamidobenzene;
4–Cyclopropoxy-1-pentafluorophenylsulfonamidobenzene;
3-Fluoro-4-cyclopropoxy-1-pentafluorophenylsulfonamidobenzene;
3-Hydroxy-4-cyclopropoxy-1-pentafluorophenylsulfonamidobenzene;
1-Hydroxy-2,3-methylenedioxy-5-pentafluorophenylsulfonamidobenzene;
1-Hydroxy-2,3-ethylenedioxy-5-pentafluorophenylsulfonamidobenzene;
1-Hydroxy-2,3-carbodioxy-5-pentafluorophenylsulfonamidobenzene;
1,3-Dihydroxy-2-ethoxy-5-pentafluorophenylsulfonamidobenzene;
1-Pentafluorophenylsulfonylindole;
1-Pentafluorophenylsulfonyl(2,3-dihydro)indole;
1-Pentafluorophenylsulfonyl(1,2-dihydro)quinoline;
1-Pentafluorophenylsulfonyl(1,2,3,4-tetrahydro)quinoline;
3,4-Difluoro-1-pentafluorophenylsulfonamidobenzene;
4-Trifluoromethoxy-1-pentafluorophenylsulfonamidobenzene;
2-Chloro-5-pentafluorophenylsulfonamidopyridine;
2-Hydroxy-1-methoxy-4-[N-5-hydroxypent-1-yl)pentafluorophenyl-sulfonamido]benzene;
4-(1,1-Dimethyl)ethoxy-1-pentafluorophenylsulfonamidobenzene;
1-Bromo-3-hydroxy-4-methoxy-1-pentafluorophenylsulfonamidobenzene;
2-Bromo-4-methoxy-5-hydroxy-1-pentafluorophenylsulfonamidobenzene;
1-Bromo-4-fluoro-5-methoxy-2-pentafluorophenylsulfonamidobenzene;
3-Chloro-1-pentafluorophenylsulfonamidobenzene;
4-Chloro-1-pentafluorophenylsulfonamidobenzene;
3-Nitro-1-pentafluorophenylsulfonamidobenzene;
4-Methoxy-1-pentafluorophenylsulfonamido-3-(trifluoromethyl)benzene;
4-Methoxy-1-[N-(2-propenyl)pentafluorophenylsulfonamido]benzene;
1-(N-(3-Butenyl)pentafluorophenylsulfonamido)-4-methoxybenzene;
4-Methoxy-1-(N-(4-pentenyl)pentafluorophenylsulfonamido)benzene;
1-[N-(2,3-Dihydroxypropyl)pentafluorophenylsulfonamido]-4-methoxy-benzene;
1-(N-(3,4-Dihydroxybutyl)pentafluorophenylsulfonamido)-4-methoxybenzene;
1-(N-(4,5-Dihydroxypentyl)pentafluorophenylsulfonamido)-4-methoxybenzene;
1-(N-(4-hydroxybutyl)pentafluorophenylsulfonamido)-4-methoxybenzene;
4-Methoxy-1-(N-(5-hydroxypentyl)pentafluorophenylsulfonamido)-benzene;
3-Amino-4-methoxy-1-pentafluorophenylsulfonamidobenzene;
4-Butoxy-1-pentafluorophenylsulfonamidobenzene;
1-Pentafluorophenylsulfonamido-4-phenoxybenzene;
6-Pentafluorophenylsulfonamidoquinoline;
2,3-Dihydro-5-pentafluorophenylsulfonamidoindole;
5-Pentafluorophenylsulfonamidobenzo[a]thiophene;
5-Pentafluorophenylsulfonamidobenzo[a]furan;
3-Hydroxy-4-(1-propenyl)-1-pentafluorophenylsulfonamidobenzene;
4-Benzyloxy-1-pentafluorophenylsulfonamidobenzene;
4-Methylmercapto-1-pentafluorophenylsulfonamidobenzene;
2-Methoxy-1-pentafluorophenylsulfonamidobenzene;
4-Allyloxy-1-pentafluorophenylsulfonamidobenzene;
1-Pentafluorophenylsulfonamido-4-propoxybenzene;
4-(1-Methyl)ethoxy-1-pentafluorophenylsulfonamidobenzene;
1,2-Methylenedioxy-4-pentafluorophenylsulfonamidobenzene;
1,2-Dimethoxy-4-pentafluorophenylsulfonamidobenzene;
4(N,N-Diethylamino)-1-pentafluorophenylsulfonamidobenzene;
4-Amino-1-pentafluorophenylsulfonamidobenzene;
Pentafluorophenylsulfonamidobenzene;
5-Pentafluorophenylsulfonamidoindazole;
4-(N,N-Dimethylamino)-1-(N-methylpentafluorophenylsulfonamido)-benzene;
1,2-Dihydroxy-4-pentafluorophenylsulfonamidobenzene;
3,5-Dimethoxy-1-pentafluorophenylsulfonamidobenzene;
3-Ethoxy-1-pentafluorophenylsulfonamidobenzene;
7-Hydroxy-2-pentafluorophenylsulfonamidonaphthalene;
3-Phenoxy-1-pentafluorophenylsulfonamidobenzene;
4-(1-Morpholino)-1-pentafluorophenylsulfonamidobenzene;
5-Pentafluorophenylsulfonamido-1,2,3-trimethoxybenzene;
2-Hydroxy-1,3-methoxy-5-pentafluorophenylsulfonamidobenzene;
1,2-Dihydroxy-3-methoxy-5-pentafluorophenylsulfonamidobenzene;

5-Pentafluorophenylsulfonamido-1,2,3-trihydroxybenzene;
3-Hydroxy-5-methoxy-1-pentafluorophenylsulfonamidobenzene;
3,5-Dihydroxy-1-pentafluorophenylsulfonamidobenzene;
2-Fluoro-1-methoxy-4-(N-methylpentafluorophenylsulfonamido)benzene;
4-(N,N-Dimethylamino)-1-pentafluorophenylsulfonamidobenzene, hydrochloride;
2-Methoxy-5-pentafluorophenylsulfonamidopyridine; and
2-Anilino-3-pentafluorophenylsulfonamidopyridine.

Examples of the most preferred pharmaceutical compositions and compounds of the subject pharmaceutical methods include:
4-(N,N-Dimethylamino)-1-pentafluorophenylsulfonamidobenzene;
3-(N,N-Dimethylamino)-1-pentafluorophenylsulfonamidobenzene;
1,2-Ethylenedioxy-4-pentafluorophenylsulfonamidobenzene;
2-Hydroxy-1-methoxy-4-pentafluorophenylsulfonamidobenzene;
2-Fluoro-1-methoxy-4-pentafluorophenylsulfonamidobenzene;
2-Hydroxy-1-methoxy-4-pentafluorophenylsulfonamidobenzene, sodium salt;
2-Hydroxy-1-methoxy-4-pentafluorophenylsulfonamidobenzene, potassium salt;
2-Fluoro-1-methoxy-4-pentafluorophenylsulfonamidobenzene, sodium salt;
2-Fluoro-1-methoxy-4-pentafluorophenylsulfonamidobenzene, potassium salt;
4-Methoxy-1-pentafluorophenylsulfonamidobenzene;
3-Hydroxy-1-pentafluorophenylsulfonamidobenzene;
4-Hydroxy-1-pentafluorophenylsulfonamidobenzene;
1,2-Dimethyl-4-pentafluorophenylsulfonamidobenzene;
5-Pentafluorophenylsulfonamidoindole;
4-Ethoxy-1-pentafluorophenylsulfonamidobenzene;
3-Methoxy-1-pentafluorophenylsulfonamidobenzene;
2-Bromo-1-methoxy-4-pentafluorophenylsulfonamidobenzene;
2-Chloro-1-methoxy-4-pentafluorophenylsulfonamidobenzene;
2-Bromo-3-hydroxy-4-methoxy-1-pentafluorophenylsulfonamidobenzene;
2-Bromo-4-methoxy-5-hydroxy-1-pentafluorophenylsulfonamidobenzene;
1-Bromo-4-fluoro-5-methoxy-2-pentafluorophenylsulfonamidobenzene;
4-Chloro-1-pentafluorophenylsulfonamidobenzene; and
3-Amino-4-methoxy-1-pentafluorophenylsulfonamidobenzene.

The invention provides for certain novel compounds of general Formula I that possess one or more valuable biological activities such as a pharmacologic, toxicologic, metabolic, etc.
Exemplary compounds of this embodiment of the invention include:
2-Fluoro-1-methoxy-4-pentafluorophenylsulfinamidobenzene;
4-Dimethylamino-1-pentafluorophenylsulfinamidobenzene;
4-Methyl-6-methoxy-2-pentafluorophenylsulfonamidopyrimidine;
4,6-Dimethoxy-2-pentafluorophenylsulfonamidopyrimidine;
2-Pentafluorophenylsulfonamidothiophene;
3-Pentafluorophenylsulfonamidothiophene;
3-Pentafluorophenylsulfonamidopyridine;
4-Pentafluorophenylsulfonamidopyridine;
4-(N,N,-Dimethylammonio)-1-(N-ethylpentafluorophenylsulfonamido) benzene;
4-tert-Butoxy-1-pentafluorophenylsulfonamidobenzene;
3-tert-Butoxy-1-pentafluorophenylsulfonamidobenzene;
2-tert-Butoxy-1-pentafluorophenylsulfonamidobenzene;
4-Isopropoxy-1-pentafluorophenylsulfonamidobenzene;
3-Isopropoxy-1-pentafluorophenylsulfonamidobenzene;
2-Isopropoxy-1-pentafluorophenylsulfonamidobenzene;
2-Methoxy-1,3-difluoro-5-pentafluorophenylsulfonamidobenzene;
1-Hydroxy-2,3-methylenedioxy-5-pentafluorophenylsulfonamidobenzene;
1-Hydroxy-2,3-ethylenedioxy-5-pentafluorophenylsulfonamidobenzene;
1-Hydroxy-2,3-carbodioxy-5-pentafluorophenylsulfonamidobenzene;
1,3-Dihydroxy-2-ethoxy-5-pentafluorophenylsulfonamidobenzene;
1-Pentafluorophenylsulfonylindole;
1-Pentafluorophenylsulfonyl(2,3-dihydro)indole;
1-Pentafluorophenylsulfonyl(1,2-dihydro)quinoline;
1-Pentafluorophenylsulfonyl(1,2,3,4-tetrahydro)quinoline;
3,4-Difluoro-1-pentafluorophenylsulfonamidobenzene;
4-Trifluoromethoxy-1-pentafluorophenylsulfonamidobenzene;
2-Chloro-5-pentafluorophenylsulfonamidopyridine;
2-Hydroxy-1-methoxy-4-[N-5-hydroxypent-1-yl)pentafluorophenyl-sulfonamido]benzene;
4-(1,1-Dimethyl)ethoxy-1-pentafluorophenylsulfonamidobenzene;
1-Bromo-3-hydroxy-4-methoxy-1-pentafluorophenylsulfonamidobenzene;
2-Bromo-4-methoxy-5-hydroxy-1-pentafluorophenylsulfonamidobenzene;
1-Bromo4-fluoro-5-methoxy-2-pentafluorophenylsulfonamidobenzene;
3-Chloro-1-pentafluorophenylsulfonamidobenzene;
4-Chloro-1-pentafluorophenylsulfonamidobenzene;
3-Nitro-1-pentafluorophenylsulfonamidobenzene;
4-Methoxy-1-pentafluorophenylsulfonamido-3-(trifluoromethyl)benzene;
4-Methoxy-1-[N-(2-propenyl)pentafluorophenylsulfonamido]benzene;
1-(N-(3-Butenyl)pentafluorophenylsulfonamido)-4-methoxybenzene;
4-Methoxy-1-(N-(4-pentenyl)pentafluorophenylsulfonamido)benzene;
1-[N-(2,3-Dihydroxypropyl)pentafluorophenylsulfonamido]-4-methoxy-benzene;
1-(N-(3,4-Dihydroxybutyl)pentafluorophenylsulfonamido)-4-methoxybenzene;
1-(N-(4,5-Dihydroxypentyl)pentafluorophenylsulfonamido)-4-methoxybenzene;
1-(N-(4-hydroxybutyl)pentafluorophenylsulfonamido)-4-methoxybenzene;
4-Methoxy-1-(N-(5-hydroxypentyl)pentafluorophenylsulfonamido)-benzene;
3-Amino-4-methoxy-1-pentafluorophenylsulfonamidobenzene;
4-Butoxy-1-pentafluorophenylsulfonamidobenzene;
1-Pentafluorophenylsulfonamido-4-phenoxybenzene;
4-Benzyloxy-1-pentafluorophenylsulfonamidobenzene;
4-Methylmercapto-1-pentafluorophenylsulfonamidobenzene;
2-Methoxy-1-pentafluorophenylsulfonamidobenzene;
4-Allyloxy-1-pentafluorophenylsulfonamidobenzene;

1-Pentafluorophenylsulfonamido-4-propoxybenzene;
4-(1-Methyl)ethoxy-1-pentafluorophenylsulfonamidobenzene;
1,2-Methylenedioxy-4-pentafluorophenylsulfonamidobenzene;
1,2-Dimethoxy-4-pentafluorophenylsulfonamidobenzene;
4-(N,N-Diethylamino)-1-pentafluorophenylsulfonamidobenzene;
4-Amino-1-pentafluorophenylsulfonamidobenzene;
Pentafluorophenylsulfonamidobenzene;
5-Pentafluorophenylsulfonamidoindazole;
4-(N,N-Dimethylamino)-1-(N-methylpentafluorophenylsulfonamido)-benzene;
1,2-Dihydroxy-4-pentafluorophenylsulfonamidobenzene;
3,5-Dimethoxy-1-pentafluorophenylsulfonamidobenzene;
3-Ethoxy-1-pentafluorophenylsulfonamidobenzene;
7-Hydroxy-2-pentafluorophenylsulfonamidonaphthalene;
3-Phenoxy-1-pentafluorophenylsulfonamidobenzene;
4-(1-Morpholino)-1-pentafluorophenylsulfonamidobenzene;
5-Pentafluorophenylsulfonamido-1,2,3-trimethoxybenzene;
2-Hydroxy-1,3-methoxy-5-pentafluorophenylsulfonamidobenzene;
1,2-Dihydroxy-3-methoxy-5-pentafluorophenylsulfonamidobenzene;
5-Pentafluorophenylsulfonamido-1,2,3-trihydroxybenzene;
4–Cyclopropoxy-1-pentafluorophenylsulfonamidobenzene;
3-Fluoro-4-cyclopropoxy-1-pentafluorophenylsulfonamidobenzene;
6-Pentafluorophenylsulfonamidoquinoline;
2,3-Dihydro-5-pentafluorophenylsulfonamidoindole;
5-Pentafluorophenylsulfonamidobenzo[a]thiophene;
5-Pentafluorophenylsulfonamidobenzo[a]furan;
3-Hydroxy-4-(1-propenyl)-1-pentafluorophenylsulfonamidobenzene;
3-Hydroxy-5-methoxy-1-pentafluorophenylsulfonamidobenzene;
3,5-Dihydroxy-1-pentafluorophenylsulfonamidobenzene;
2-Fluoro-1-methoxy-4-(N-methylpentafluorophenylsulfonamido)benzene;
4-(N,N-Dimethylamino)-1-pentafluorophenylsulfonamidobenzene, hydrochloride; and,
2-Anilino-3-pentafluorophenylsulfonamidopyridine.

Preferred compounds of this embodiment of the invention have specific pharmacological properties. Examples of the most preferred compounds of this embodiment of the invention include:
4-(N,N-Dimethylamino)-1-pentafluorophenylsulfonamidobenzene;
3-(N,N-Dimethylamino)-1-pentafluorophenylsulfonamidobenzene;
1,2-Ethylenedioxy-4-pentafluorophenylsulfonamidobenzene;
2-Hydroxy-1-methoxy-4-pentafluorophenylsulfonamidobenzene;
2-Fluoro-1-methoxy-4-pentafluorophenylsulfonamidobenzene;
2-Hydroxy-1-methoxy-4-pentafluorophenylsulfonamidobenzene, sodium salt;
2-Hydroxy-1-methoxy-4-pentafluorophenylsulfonamidobenzene, potassium salt;
2-Fluoro-1-methoxy-4-pentafluorophenylsulfonamidobenzene, sodium salt;
2-Fluoro-1-methoxy-4-pentafluorophenylsulfonamidobenzene, potassium salt;
4-Methoxy-1-pentafluorophenylsulfonamidobenzene;
3-Hydroxy-1-pentafluorophenylsulfonamidobenzene;
4-Hydroxy-1-pentafluorophenylsulfonamidobenzene;
1,2-Dimethyl-4-pentafluorophenylsulfonamidobenzene;
5-Pentafluorophenylsulfonamidoindole;
4-Ethoxy-1-pentafluorophenylsulfonamidobenzene;
3-Methoxy-1-pentafluorophenylsulfonamidobenzene;
2-Bromo-1-methoxy-4-pentafluorophenylsulfonamidobenzene;
2-Chloro-1-methoxy-4-pentafluorophenylsulfonamidobenzene;
2-Bromo-3-hydroxy-4-methoxy-1-pentafluorophenylsulfonamidobenzene;
2-Bromo-4-methoxy-5-hydroxy-1-pentafluorophenylsulfonamidobenzene;
1-Bromo-4-fluoro-5-methoxy-2-pentafluorophenylsulfonamidobenzene;
4-Chloro-1-pentafluorophenylsulfonamidobenzene; and
3-Amino-4-methoxy-1-pentafluorophenylsulfonamidobenzene.

Synthesis

Scheme I

Syntheses of pentafluorophenylsulfonamides, sulfonic esters, sulfinamides, and sulfinic esters

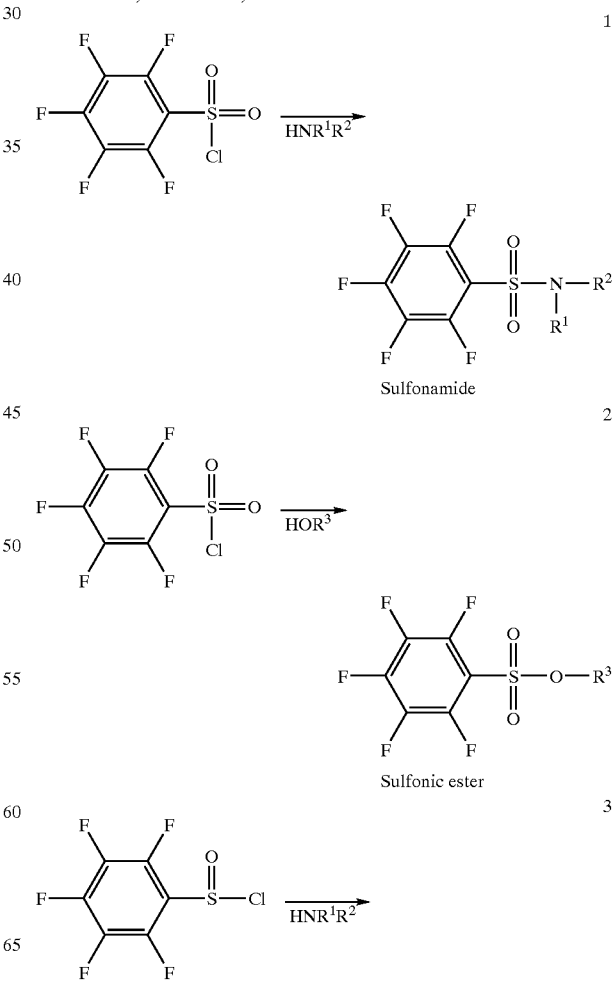

-continued

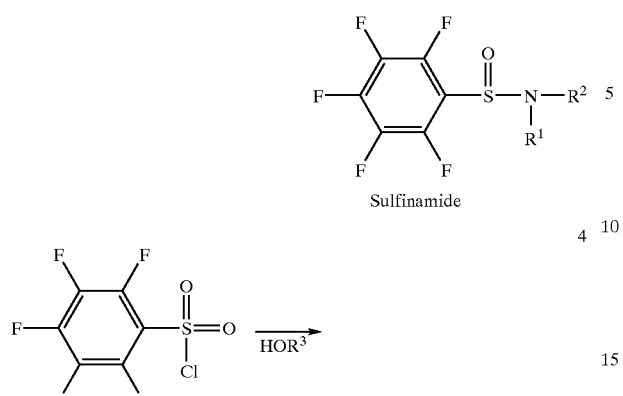

Sulfinamide

Sulfonic ester

Scheme II

Alternative synthesis of N,N-disubstituted pentafluorophenylsulfonamides.

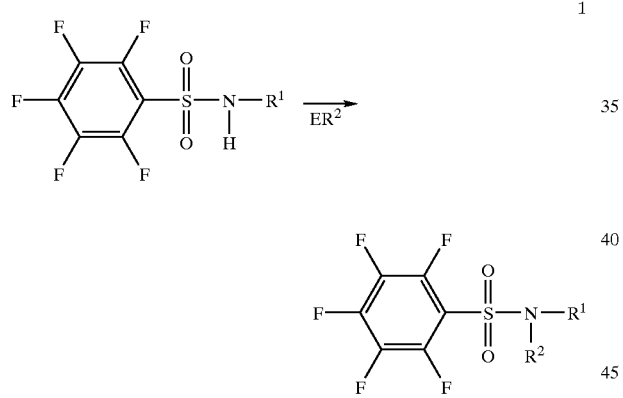

Scheme III

Synthesis of phenols

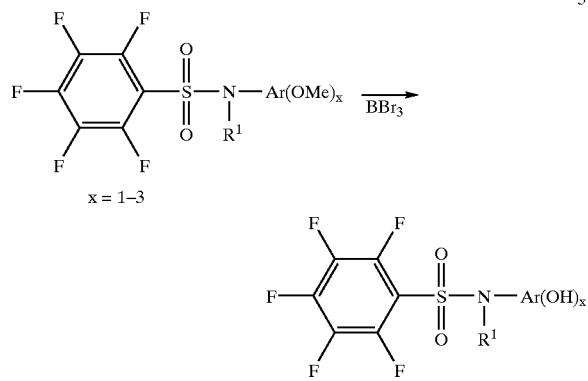

x = 1–3

Scheme IV

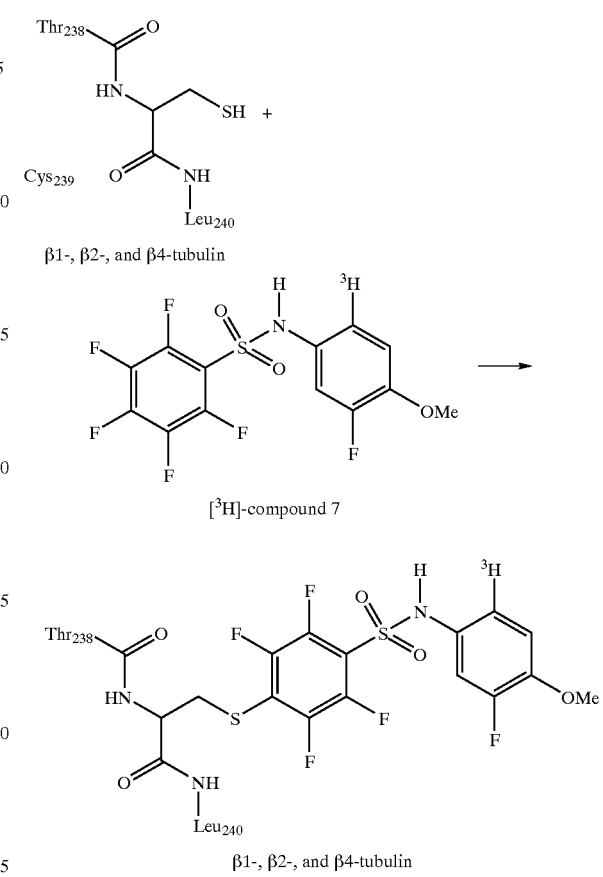

β1-, β2-, and β4-tubulin

[$^3$H]-compound 7

β1-, β2-, and β4-tubulin

The invention provides methods of making the subject compounds and compositions. In one general embodiment, the methods involve combining pentafluorophenylsulfonyl chloride with an amine having the general formula $R^1R^2NH$ under conditions whereby the pentafluorophenylsulfonyl chloride and amine react to form the desired compound, and isolating the compound.

Compounds with the generic structure 1 or 3 (Scheme I) may be prepared by reacting the appropriate starting amine in a solvent such as tetrahydrofuran (THF), dimethylformamide (DMF), ether, toluene or benzene in the presence of a base such as pyridine, p-dimethylaminopyridine, triethylamine, sodium carbonate or potassium carbonate and pentafluorophenylsulfonyl chloride or pentafluorophenylsulfinyl chloride, respectively. Pyridine itself may also be used as the solvent. Preferred solvents are pyridine and DMF and preferred bases are pyridine, triethylamine, and potassium carbonate. This reaction can be carried out at a temperature range of 0° C. to 100° C., conveniently at ambient temperature.

Compounds of the generic structure 1 can also be obtained by treating the starting sulfonamide (Scheme II) with a base such as LDA, NaH, dimsyl salt, alkyl lithium, potassium carbonate, under an inert atmosphere such as argon or nitrogen, in a solvent such as benzene, toluene, DMF or THF with an alkylating group containing a leaving group such a Cl, Br, I, MsO—, TsO—, TFAO—, represented by E in Scheme II. A preferred solvent for this reaction is THF and the preferred base is lithium bis(trimethylsilyl) amide. This reaction can be carried out at a temperature range of 0° C. to 100° C., conveniently at ambient temperature.

Sulfonic esters (2) and sulfinic esters (4) may be prepared by reacting the appropriate starting phenol in a solvent such as THF, DMF, toluene or benzene in the presence of a base such as pyridine, triethylamine, sodium carbonate, potassium carbonate or 4-dimethylaminopyridine with pentafluorophenylsulfonyl chloride or pentafluorophenylsulfinyl chloride, respectively. Pyridine itself may also be used as the solvent. Preferred solvents are pyridine and DMF and preferred bases are sodium carbonate and potassium carbonate. This reaction can be carried out at a temperature range of 0° C. to 100° C., conveniently at ambient temperature.

Compounds of the general structure 5, in which Ar is an aromatic group and x is from one to three, can be obtained from the corresponding methyl ethers (Scheme III) by reaction with boron tribromide in a solvent of low polarity such as hexanes or $CH_2Cl_2$ under an inert atmosphere at a temperature ranging from −45° to 30° C. In a preferred embodiment, the reaction is carried out in $CH_2Cl_2$ at about 30° C.

Occasionally, the substrates for the transformations shown in Schemes I–III may contain functional groups (for example, amino, hydroxy or carboxy) which are not immediately compatible with the conditions of the given reaction. In such cases, these groups may be protected with a suitable protective group, and this protective group removed subsequent to the transformation to give the original functionality using well know procedures such as those illustrated in T. W. Greene and P. G. M. Wuts, Protective Groups in Organic Synthesis, Second Edition, John Wiley & Sons, Inc., 1991.

The compounds used as initial starting materials in this invention may be purchased from commercial sources or alternatively are readily synthesized by standard procedures which are well know to those of ordinary skill in the art.

Some of the compounds of formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of formula I which are acidic or basic in nature can form a wide variety of salts with various inorganic and organic bases or acids, respectively. These salts must be pharmacologically acceptable for administration to mammals. Salts of the acidic compounds of this invention are readily prepared by treating the acid compound with an appropriate molar quantity of the chosen inorganic or organic base in an aqueous or suitable organic solvent and then evaporating the solvent to obtain the salt. Acid addition salts of the basic compounds of this invention can be obtained similarly by treatment with the desired inorganic or organic acid and subsequent solvent evaporation and isolation.

The compounds of the invention may be labeled in a variety of ways. For example, the compounds may be provided as radioactive isotopes; for example, tritium and the $^{14}C$-isotopes. Similarly, the compounds may be advantageously joined, covalently or noncovalently, to a wide variety of joined compounds which may provide pro-drugs or function as carriers, labels, adjuvents, coactivators, stabilizers, etc. Hence, compounds having the requisite structural limitations encompass such compounds joined directly or indirectly (e.g. through a linker molecule), to such joined compounds.

A wide variety of indications may be treated, either prophylactically or therapeutically, with the compounds and compositions of the present invention. For example, the subject compounds and compositions have been found to be effective modulators of cell proliferation. Limitation of cell growth is effected by contacting a target cell, in or ex vivo, with an effective amount of one or more of the subject compositions or compounds. Compounds may be assayed for their ability to modulate cellular proliferation using cell and animal models to evaluate cell growth inhibition and cytotoxicity, which models are known in the art, but are exemplified by the method of S. A. Ahmed et al. (1994) J. Immunol. Methods 170: 211–224, for determining the effects of compounds on cell growth.

Conditions amenable to treatment by the compounds and compositions of the present invention include any state of undesirable cell growth, including various neoplastic diseases, abnormal cellular proliferations and metastatic diseases, where any of a wide variety of cell types may be involved, including cancers such as Kaposi's sarcoma, Wilms tumor, lymphoma, leukemia, myeloma, melanoma, breast, ovarian, lung, etc, and others such as cystic disease, cataracts, psoriasis, etc. Other conditions include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. trypanosomes, fungi, etc) are also subject to selective proliferative control using the subject compositions and compounds.

Many of the subject compounds have been shown to bind to the β-subunit of tubulin and interfere with normal tubulin function. Hence, the compounds provide agents for modulating cytoskeletal structure and/or function. Preferred compounds bind irreversibly or covalently, and hence provide enhanced application over prior art microtubule disruptors such as colchicine. The compositions may be advantageously combined and/or used in combination with other antiproliferative chemotherapeutic agents, different from the subject compounds (see Margolis et al. (1993) U.S. Pat. No. 5,262,409). Additional relevant literature includes: Woo et al. (1994) WO94/08041; Bouchard et al. (1996) WO96/13494; Bombardelli et al. (1996) WO96/11184; Bonura et al. (1992) WO92/15291.

Analysis

The subject compositions were demonstrated to have pharmacological activity in in vitro and in vivo assays, e.g. are capable of specifically modulating a cellular physiology to reduce an associated pathology or provide or enhance a prophylaxis. Preferred compounds display specific toxicity to various types of cells. Certain compounds and compositions of the present invention exert their cytotoxic effects by interacting with cellular tubulin. For certain preferred compounds and compositions of the present invention, that interaction is covalent and irreversible. For example, exposure of a wide variety of tissue and cell samples, e.g. human breast carcinoma MCF7 cells, to tritiated forms of these preferred compounds, e.g. Compound 7 (Example 72), results in the irreversible labeling of only one detectable cellular protein, which was found to be tubulin. This protein is a key component of microtubules, which constitute the cytoskeleton and also play critical roles in many other aspects of the cell's physiology, including cell division. The labeling of tubulin by the subject preferred compounds is also shown to be dose-dependent. The site of covalent binding on tubulin is identified as Cysteine-239 on the β-tubulin chain. The same Cys-239 residue is selectively covalently modified when present in a wide variety of Cys-239 containing β-tubulin petides (e.g. Ser-234 to Met-267) provided in vitro or in vivo. One embodiment of these preferred compounds provides the binding mechanism shown in Scheme IV, namely, displacement of the para-fluorine atom by the thiol group of Cys-239. Consistent with the ability of these compounds to bind to β-tubulin, treatment of a wide variety of cell and tissue types with various concentrations of the compounds resulted in widespread, irreversible disruption of the cytoskeleton of most cells.

As discribed inter alia in Luduena (1993) Mol Biol of the Cell 4, 445–457, tubulin defines a family of heterodimers of two polypeptides, designated α and β. Moreover, animals express multiple forms (isotypes) of each α and β polypeptides from multiple a and β genes. Many β isotypes comprise a conserved cysteine, Cys-239 (of human β2 tubulin: because of upstream sequence variations, the absolute position of Cys-239 is subject to variation, though Cys-239 is readily identified by those in the art by its relative position (i.e. context within encompassing consensus sequence, e.g. at least 8, preferably 12, more preferably 16, most preferably 20 residue consensus peptide region of the isotype or fragment thereof, which region contains Cys-239). By selective binding to Cys-239 is meant that Cys-239 is preferentially bound relative to all other residues, including cysteins of the protein, by at least at least a factor of 2, preferably 10, more preferably 100, most preferably 1,000. In a particularly prefered embodiment, Cys-239 is substantially exclusively and preferably exclusive bound. By selective binding to or modification of tubulin is meant that tubulin is preferentially modified relative to all other proteins, by at least a factor of 2, preferably 10, more preferably 100, most preferably 1,000. In a particularly prefered embodiment, tubulin is substantially exclusively and preferably exclusive modified.

Compounds may be evaluated in vitro for their ability to inhibit cell growth, for example, as described in S. A. Ahmed et al. (1994) J. Immunol. Methods 170:211–224. In addition, established animal models to evaluate antiproliferative effects of compounds are known in the art. For example, several of the compounds disclosed herein are shown to inhibit the growth of human tumors, including MDR and taxol and/or vinblastine-restistant tumors, grafted into immunodeficient mice (using methodology similar to that reported by J. Rygaard and C. O. Povlsen (1969) Acta Pathol. Microbiol. Scand. 77:758–760, and reviewed by B. C. Giovanella and J. Fogh (1985) Adv. Cancer Res. 44:69–120.

Formulation and Administration

The invention provides methods of using the subject compounds and compositions to treat disease or provide medicinal prophylaxis, to slow down and/or reduce the growth of tumors, to treat bacterial infections, etc. These methods generally involve contacting cells with or administering to the host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other antiproliferative therapeutic or prophylactic agents, different from the subject compounds. In many instances, administration in conjunction with the subject compositions enhances the efficacy of such agents. Exemplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof.

The compounds and compositions also find use in a variety of in vitro and in vivo assays, including diagnostic assays. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H NMR spectra were recorded on a Varian Gemini 400 MHz NMR spectrometer. Significant peaks are tabulated in the order: multiplicity (s, singlet; d, doublet; t, triplet; q, quartet; m, multiplet), coupling constant(s) in Hertz, number of protons. Electron Ionization (EI) mass spectra were

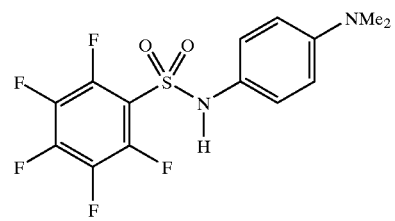

recorded on a Hewlett Packard 5989A mass spectrometer. Fast Atom Bombardment (FAB) mass spectroscopy was carried out in a VG analytical ZAB 2-SE high field mass spectrometer. Mass spectroscopy results are reported as the ratio of mass over charge, and the relative abundance of the ion is reported in parentheses.

Example 1

4-(N,N-Dimethylamino)-1-pentafluorophenylsulfonamidobenzene. To N,N-dimethyl-1,4-phenylalanine dihydrochloride (3 g, 14.6 mmol) suspended in pyridine (50 mL) at 0° C. under argon was added dropwise pentafluorophenylsulfonyl chloride (2.38 mL, 16 mmol). The reaction mixture was stirred for 30 min at 0° C. and allowed to warm to ambient temperature. The reaction mixture was stirred at room temperature for 3 h. The volume of the mixture was then reduced to 10 mL under reduced pressure. The mixture was diluted with ethyl acetate and the reaction quenched with water. The layers were separated and the aqueous layer extracted twice with ethyl acetate. The organic layers were combined and washed with brine and dried with $MgSO_4$. The solvent was evaporated and the residue purified by chromatography on silica, eluting with $CH_2Cl_2$. The title product was obtained as a white solid in 63% yield (3.4 g). $^1H$ NMR ($CDCl_3$): 7.01(d, J=8.9 Hz, 2H), 6.77(s, 1H), 6.59(d, J=8.3 Hz, 2H), 2.92 ppm (s, 6H). FAB m/z (relative abundance): 367(100%, M+H+), 135(30%), 121(25%). Anal. calcd. for $C_{14}H_{11}F_5N_2O_2S$: C, 45.95; H, 3.03; N, 7.65. Found C, 45.83; H, 2.99; N, 7.62

Example 2

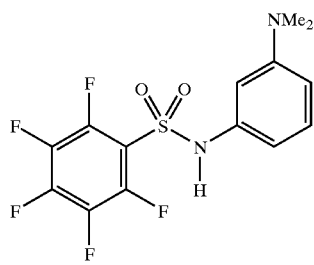

3-(N,N-Dimethylamino)-1-pentafluorophenylsulfonamidobenzene. $^1H$ NMR ($CDCl_3$): 7.12(t, J=8 Hz, 1H), 7.05(s, 1H), 6.57(s, 1H) 6.53(d, J=8 Hz, 1H), 6.40(d, J=8 Hz, 1H), 2.94 ppm (s, 6H). FAB m/z: 366 (100%, M+). The compound was prepared by a protocol similar to that of example 1 by replacing N,N-dimethyl-1,4-phenyldiamine dihydrochloride with 3-(N,N-dimethylamino)aniline.

Example 3

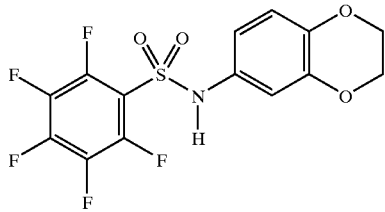

1,2-Ethylenedioxy-4-pentafluorophenylsulfonamidobenzene. $^1H$ NMR ($CDCl_3$): 6.97(s, 1H), 6.76(d, J=8.6 Hz, 1H), 6.72(d, J=2.6 Hz, 1H), 6.62(dd, J=8.6, 2.6 Hz, 1H), 4.21 ppm (s, 4H). FAB m/z: 381(100%, M+H+). Anal calcd. for $C_{14}H_8F_5NO_4S$: C, 44.09; H, 2.12; N, 3.68; S, 8.39. Found: C, 43.83; H, 2.19; N, 3.62; S, 8.20. The compound was prepared by a protocol similar to that of example 1 by replacing N,N-dimethyl-1,4-phenyldiamine dihydrochloride with 3,4-ethylenedioxyaniline.

Example 4

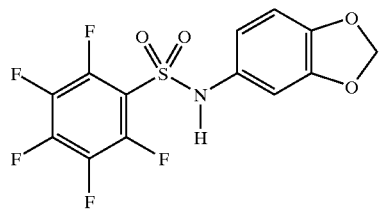

1,2-Methylenedioxy-4-pentafluorophenylsulfonamidobenzene. $^1H$ NMR ($CDCl_3$): 6.85(s, 1H), 6.78 (s, 1H), 6.70(d, J=8 Hz, 1H), 6.57(d, J=8 Hz, 1H), 5.97 ppm(s, 2H). The compound was prepared by a protocol similar to that of example 1 by replacing N,N-dimethyl-1,4-phenyldiamine dihydrochloride with 3,4-methylenedioxyaniline.

Example 5

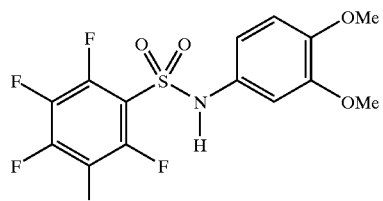

1,2-Dimethoxy-4-pentafluorophenylsulfonamidobenzene. $^1H$ NMR ($CDCl_3$): 6.98(s, 1H), 6.85(d, 1H), 6.74(d, 1H), 6.60(dd, 1H), 3.85(s, 3H), 3.83 ppm (s, 3H). EI, m/z: 383(50, M+), 152(100). The compound was prepared by a protocol similar to that of example 1 by replacing N,N-dimethyl-1,4-phenyldiamine dihydrochloride with 3,4-dimethoxyaniline.

Example 6

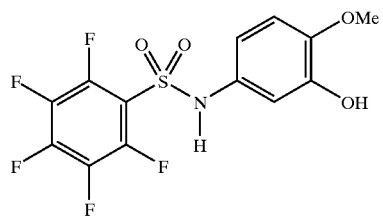

2-Hydroxy-1-methoxy-4-pentafluorophenylsulfonamidobenzene. $^1H$ NMR ($CDCl_3$): 6.93(s, 1H), 6.7–6.8(m, 3H), 5.68(bs, 1H), 3.85 ppm(s, 3H). EI, m/z: 333(20, M+), 138(100). mp 118–120° C. The compound was prepared by a protocol similar to that of example 1 by replacing N,N-dimethyl-1,4-phenyldiamine dihydrochloride with 3-hydroxy-4-methoxyaniline.

Example 7

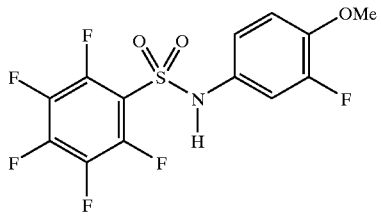

2-Fluoro-1-methoxy-4-pentafluorosulfonamidobenzene. $^1$H NMR (DMSO) 11.15 (broad s, 1H), 7.13 (t, J=9 Hz, 1H), 7.02 (dd, J=9.5 2.5 Hz, 1H), 6.94 ppm (dd, J=8.8 1.5 Hz, 1H), 3.79 ppm (s, 3H). EI, m/z: 371 (20, M$^+$), 140 (100). Anal. calcd. for $C_{13}H_7HF_6N_1O_3S_1$: C, 42.06; H, 1.90; N 3.77, S 8.64. Found: C, 42.19; H, 1.83; N 3.70; S, 8.60. Mp 118–119° C. The compound was prepared by a protocol similar to that of example 1 by replacing N,N-dimethyl-1,4-phenyldiamine dihydrochloride with 3-fluoro-p-anisidine.

Example 8

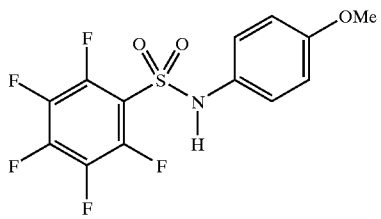

4-Methoxy-1-pentafluorophenylsulfonamidobenzene. $^1$H NMR (CDCl$_3$): 6.99 (s, 1H), 6.96(d, J=4 Hz, 2H), 6.88 (d, J=4 Hz, 2H), 3.83 ppm(s, 3H). EI, m/z: 353 (60, M$^+$), 122 (100). M.p. 102–103° C. The compound was prepared by a protocol similar to that of example 1 by replacing N,N-dimethyl-1,4-phenyldiamine dihydrochloride with 4-methoxyaniline.

Example 9

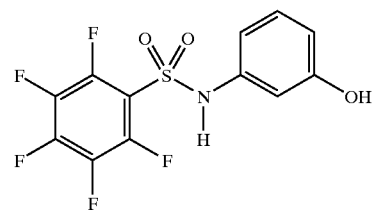

3-Hydroxy-1-pentafluorophenylsulfonamidobenzene. $^1$H NMR (CD$_3$OD): 7.15(t, J=8.1 Hz, 1H), 6.67(t, J=2.2 Hz, 1H) 6.60(dd, J=1.3 Hz, 7.8 Hz, 1H), 6.52 ppm (dd, J=2.4 Hz 8.3 Hz, 1H). EI, m/z: 339 (80, M$^+$), 256 (50), 81 (100). The compound was prepared by a protocol similar to that of example 1 by replacing N,N-dimethyl-1,4-phenyldiamine dihydrochloride with 3-hydroxyaniline.

Example 10

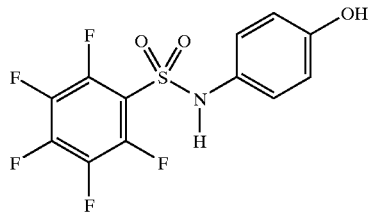

4-Hydroxy-1-pentafluorosulfonamidobenzene. $^1$H NMR (CD$_3$OD): 6.95(d, J=8.9 Hz, 2H), 6.65 ppm (d, J=8.9 Hz, 2H). EI, m/z: 339 (30, M$^+$). The compound was prepared by a protocol similar to that of example 1 by replacing N,N-dimethyl-1,4-phenyldiamine dihydrochloride with 4-hydroxyaniline.

Example 11

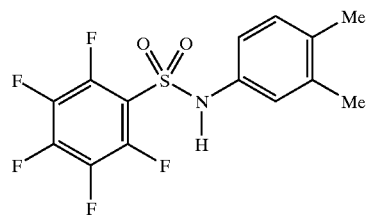

1,2-Dimethyl-4-pentafluorophenylsulfonamidobenzene. $^1$H NMR (CDCl$_3$): 7.03(d, J=7.9 Hz, 1H), 6.92(s, 1H), 6.85–6.82(m, 2H), 2.18(s, 3H), 2.16 ppm(s, 3H). The compound was prepared by a protocol similar to that of example 1 by replacing N,N-dimethyl-1,4-phenyldiamine dihydrochloride with 3,4-dimethylaniline.

Example 12

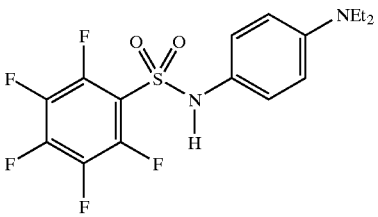

4-(N,N-Diethylamino)-1-pentafluorophenylsulfonamidobenzene. $^1$H NMR (CDCl$_3$): 6.93 (d, J=8.8 Hz, 2H), 6.78(s, 1), 6.45(d, J=8.7 Hz, 2H), 3.25(dd, J=7.0 Hz, 7.3 Hz,4H), 1.10 ppm (t, J=7.2 Hz, 6H). The compound was prepared by a protocol similar to that of example 1 by replacing N,N-dimethyl-1,4-phenyldiamine dihydrochloride with 4-(N,N-diethylamino)aniline.

Example 13

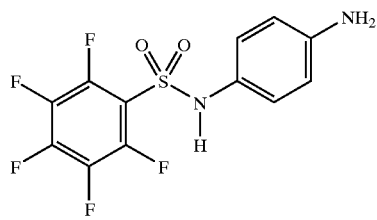

4-Amino-1-pentafluorophenylsulfonamidobenzene. $^1$H NMR (CDCl$_3$): 6.82(d, J=8.7 Hz, 2H), 6.49 ppm(d, J=8.7 Hz, 2H). EI, m/z: 338(7, M$^+$), 107(100), 80(40). The compound was prepared by a protocol similar to that of example 1 by replacing N,N-dimethyl-1,4-phenyldiamine dihydrochloride with 1,4-diaminobenzene.

Example 14

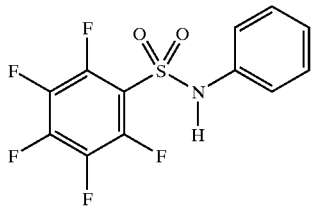

Pentafluorophenylsulfonamidobenzene. $^1$H NMR (CDCl$_3$): 7.30(d, J=8 Hz, 2H), 7.13–7.2(m, 3H), 7.0 ppm(s, 1H). EI, m/z: 323(90, M$^+$), 92(100). The compound was prepared by a protocol similar to that of example 1 by replacing N,N-dimethyl-1,4-phenyldiamine dihydrochloride with aniline.

Example 15

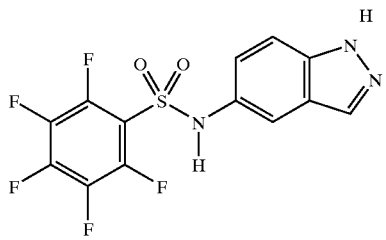

5-Pentafluorophenylsulfonamidoindazole. $^1$H NMR (CD$_3$OD): 7.98(s, 1H), 7.69(s, 1H), 7.47(d, J=8.3 Hz, 1H), 7.23 ppm(d, J=8.3 Hz, 1H). EI m/z: 364(50, M+H$^+$), 133 (100). The compound was prepared by a protocol similar to that of example 1 by replacing N,N-dimethyl-1,4-phenyldiamine dihydrochloride with 5-aminoindazole.

Example 16

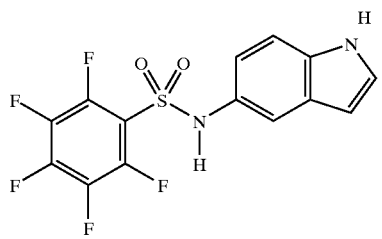

5-Pentafluorophenylsulfonamidoindole. $^1$H NMR (CDCl$_3$): 8.2(s, 1H), 7.43(s, 1H), 7.3(d, J=8 Hz, 1H), 7.22(s, 1H)), 6.98 (d, J=8 Hz, 1H), 6.92 ppm (s, 1H), 6.50 ppm(s, 1H). EI m/z: 362(M$^+$), 131(100). The compound was prepared by a protocol similar to that of example 1 by replacing N,N-dimethyl-1,4-phenyldiamine dihydrochloride with 5-aminoindole.

Example 17

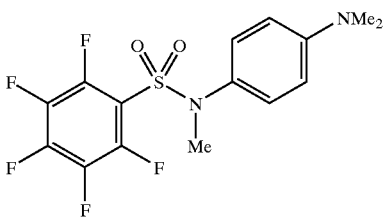

4-(N,N-Dimethylamino)-1-(N-methylpentafluorophenylsulfonanido)benzene.

4-(N,N-Dimethylamino)-1-(pentafluorophenylsulfonamido)benzene (100 mg, 0.273 mmol) was dissolved in dry THF (2.5 mL) and to the system was added under N$_2$ at room temperature a 1 M solution of lithium bis(trimethylsilyl)amide (0.274 mL). The reaction mixture was stirred for 10 min followed by addition of MeI (65 mg, 0.028 mL). The reaction mixture was stirred overnight, the solvent was evaporated under reduced pressure and the crude product purified by HPLC using silica as the stationary phase and eluting with 20% EtOAc/Hex (v/v) to afford the product as a white solid in 60% yield (62 mg). EI m/z: 380(35, M$^+$), 149(100). $^1$H NMR (CD$_3$OD) 7.05(d, J=8 Hz, 2H), 6.68(d, J=8 Hz, 2H), 3.33(s, 3H) 2.93(s, 6H). Anal. calcd. for C$_{15}$H$_{13}$F$_5$SO$_2$N$_2$: C, 47.37; H, 3.45; N, 7.37. Found: C, 47.37; H, 3.49; N, 7.32.

Example 18

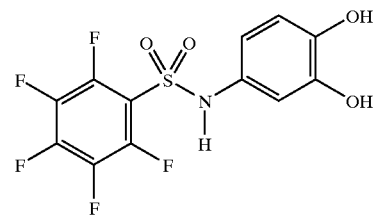

1,2-Dihydroxy-4-pentafluorophenylsulfonamidobenzene.

1-Hydroxy-2-methoxy-4-pentafluorophenylsulfonamidobenzene (250 mg, 0.678 mmol) was suspended in dry CH$_2$Cl$_2$ (5 mL) at 0° C. under nitrogen. To the mixture was added BBr₃ as a 1M solution in CH₂Cl₂ (0.746 mmol, 1.1 eq.). The mixture was warmed to ambient temperature and stirred overnight. The reaction mixture was poured over ice (75 mL) and extracted 3 times with 30 mL portions of CH₂Cl₂. The organic layer was dried with MgSO₄, and the solvent was evaporated. The crude product was purified by chromatography over silica eluting with 30% (v/v) EtOAc/Hex to afford the product as a white solid in 41% yield (98 mg). ¹H NMR (DMSO): 10.63(s, 1H), 9.15(s, 1H), 8.91(s, 1H), 6.61(d, J=9 Hz, 1H), 6.58(d, J=3 Hz, 1H), 6.39 ppm(dd, J=9 Hz 3 Hz, 1H).

Example 19

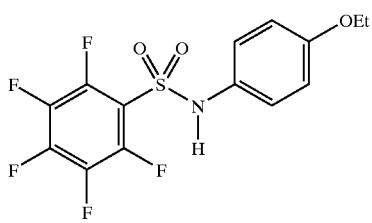

4-Ethoxy-1-pentafluorophenylsulfonamidobenzene. To a stirred solution of p-phenetidine (0.100 g, 0.729 mmol) in dimethylformamide (3.65 mL) at 25° C. was added pentafluorophenyl sulfonyl chloride (0.135 mL, 0.91 mmol), followed by sodium carbonate (0.116 g, 1.09 mmol), and the reaction mixture was stirred for 18 hours. The reaction mixture was diluted with ethyl acetate (50 mL) and washed with 20% ammonium chloride (2×20 mL) and saturated sodium chloride (2×20 mL). The organic layer was dried (sodium sulfite), and the ethyl acetate was removed under reduced pressure to yield a reddish-brown oil. Column chromatography (3:1 ethyl acetate/hexane) yielded the title compound (0.222 g, 83%). ¹H NMR (CDCl₃) 7.08 (d, J=9 Hz, 2H), 7.04 (s, 1H), 6.80 (d, J=9 Hz, 2H), 3.96 (q, J=7 Hz, 2H), 1.37 ppm (t, J=7 Hz, 2H). IR (neat) 3000–3600, 1750 cm⁻¹. EI m/z : 367(M⁺), 154, 136.

The compounds of Examples 20 through 26 were prepared by a protocol similar to that of Example 19 by replacing p-phenetidine with the appropriate amine.

Example 20

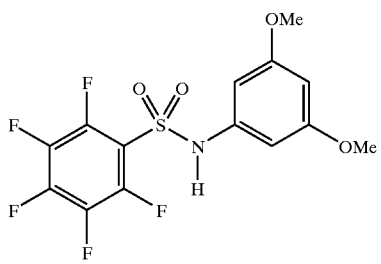

3,5-Dimethoxy-1-pentafluorophenylsulfonamidobenzene. The compound was prepared by a protocol similar to that of Example 19 by replacing p-phenetidine with 3,5-dimethoxyaniline. ¹H NMR (CDCl₃) 6.91(s, 1H), 6.32(s, 2H), 6.25(s, 1H), 3.72 ppm(s, 6H).

Example 21

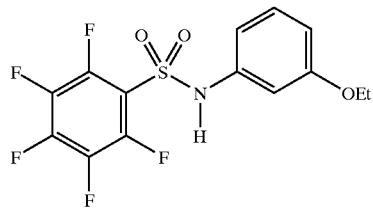

3-Ethoxy-1-pentafluorophenylsulfonamidobenzene. The compound was prepared by a protocol similar to that of Example 19 by replacing p-phenetidine with 3-ethoxyaniline. ¹H NMR (CDCl₃) 7.35 (t, J=8 Hz, 1H), 7.21(s, 1H), 6.92( s, 1H), 6.86(d, J=8 Hz, 1H), 6.83(d, J=8 Hz, 1H), 4.15( q, J=6 Hz, 2H), 1.56 ppm ( t, J=6 Hz, 3H).

Example 22

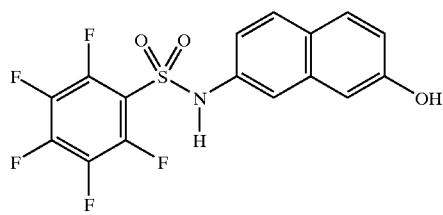

7-Hydroxy-2-pentafluorophenylsulfonamidonaphthalene. The compound was prepared by a protocol similar to that of Example 19 by replacing p-phenetidine with 2-amino-7-hydroxynaphthalene. ¹H NMR (CDCl₃) 8.15 (t, J=8 Hz, 1H), 7.55( d, J=8 Hz, 1H), 7.44 (s, 1H), 7.42 (d, J=8 Hz, 1H), 7.40 (s, 1H), 6.88 ppm (q, J=8 Hz, 1H).

Example 23

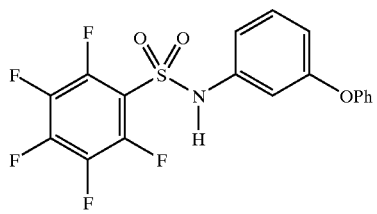

3-Phenoxy-1-pentafluorophenylsulfonamidobenzene. The compound was prepared by a protocol similar to that of Example 19 by replacing p-phenetidine with 3-phenoxyaniline. ¹H NMR (CDCl₃) 7.34 ( t, J=8 Hz, 2H), 7.26 ( t, J=8 Hz, 1H), 7.16 ( t, J=8 Hz, 1H), 6.94 (d, J=8 Hz, 2H), 6.86 (d, J=8 Hz, 1H), 6.82 (d, J=8 Hz, 1H), 6.74 (s, 1H).

Example 24

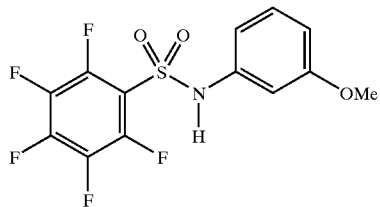

3-Methoxy-1-pentafluorophenylsulfonamidobenzene. The compound was prepared by a protocol similar to that of Example 19 by replacing p-phenetidine with 3-methoxyaniline. $^1$H NMR (CDCl$_3$) 7.20 (d, J=8 Hz, 1H, ), 6.95 (s, 1H), 6.78 (d, J=8 Hz, 1H,), 6.70 (t, J=8 Hz, 1H), 3.79 ppm (s, 1H).

Example 25

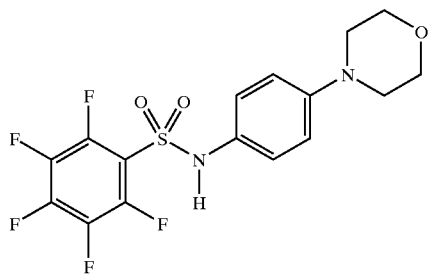

4-(1-Morpholino)-1-pentafluorophenylsulfonamidobenzene. The compound was prepared by a protocol similar to that of Example 19 by replacing p-phenetidine with 4-(1-morpholino)aniline. $^1$H NMR (CDCl$_3$) 7.09 (d, J=8 Hz, 2H), 6.85 (d, J=8 Hz, 2H), 3.85 (t, J=8 Hz, 4H), 3.15 ppm (t, J=8 Hz, 4H).

Example 26

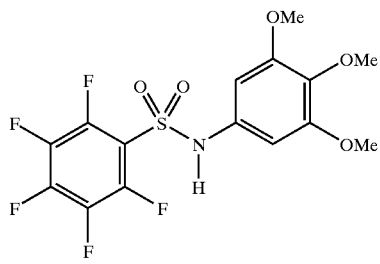

5-Pentafluorophenylsulfonamido-1,2,3-trimethoxybenzene. The compound was prepared by a protocol similar to that of Example 19 by replacing p-phenetidine with 3,4,5-trimethoxyaniline. $^1$H NMR (CDCl$_3$) 8.14 (s, 1H), 6.46 (s, 2H), 3.69 (s, 6H), 3.59 (s, 3H).

Example 27

1,3-Dimethoxy-2-hydroxy-5-pentafluorophenylsulfonamidobenzene.

1,2-Dihydroxy-3-methoxy-5-pentafluorophenylsulfonamidobenzene.

5-Pentafluorophenylsulfonamido-1,2,3-trihydroxybenzene.

1,2,3-Methoxy-5-pentafluorophenylsulfonamidobenzene (269 mg, 0.65 mmol) was suspended in dry CH$_2$Cl$_2$ (5 mL) at 0° C. under nitrogen. To the mixture was added BBr$_3$ as a 1M solution in CH$_2$Cl$_2$ (3.26 mmol, 5 eq.). The mixture was warmed to ambient temperature and stirred overnight. The reaction mixture was poured over ice (75 mL) and extracted 3 times with 30 mL portions of CH$_2$Cl$_2$. The organic layer was dried with MgSO$_4$, evaporated, and the residue was subjected to chromatography over silica eluting with 30% (v/v) EtOAc/Hex to afford the three products. The compounds of Examples 28 and 29 were prepared in a manner similar to that described above beginning with the product of Example 20 and treating it with BBr$_3$.

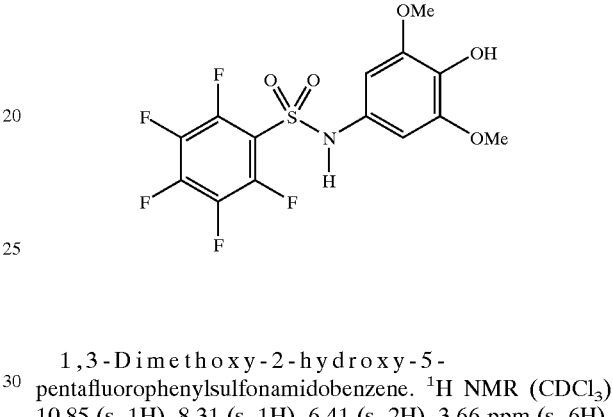

1,3-Dimethoxy-2-hydroxy-5-pentafluorophenylsulfonamidobenzene. $^1$H NMR (CDCl$_3$) 10.85 (s, 1H), 8.31 (s, 1H), 6.41 (s, 2H), 3.66 ppm (s, 6H).

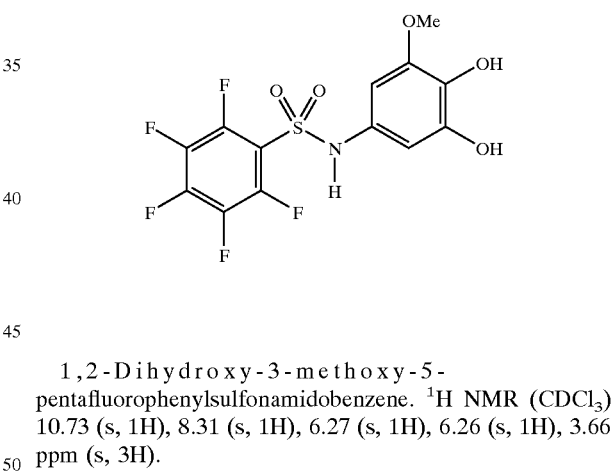

1,2-Dihydroxy-3-methoxy-5-pentafluorophenylsulfonamidobenzene. $^1$H NMR (CDCl$_3$) 10.73 (s, 1H), 8.31 (s, 1H), 6.27 (s, 1H), 6.26 (s, 1H), 3.66 ppm (s, 3H).

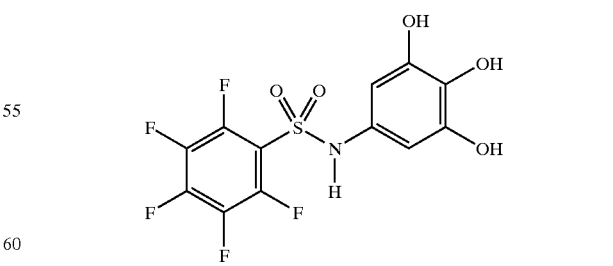

5-Pentafluorophenylsulfonamido-1,2,3-trihydroxybenzene. $^1$H NMR (CDCl$_3$) 11.0 (s, 1H), 9.03 (s, 2H), 8.06 (s, 1H), 6.13 ppm (s, 2H).

Example 28

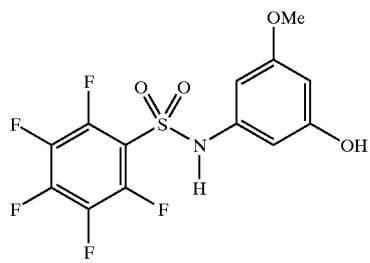

3-Hydroxy-5-methoxy-1-pentafluorophenylsulfonamidobenzene. $^1$H NMR (CDCl$_3$) 11.2 (s, 1H), 9.63 (s, 1H), 6.23 (s, 1H), 6.21 (s, 1H), 6.08 (s, 1H), 3.63 (s, 3H).

Example 29

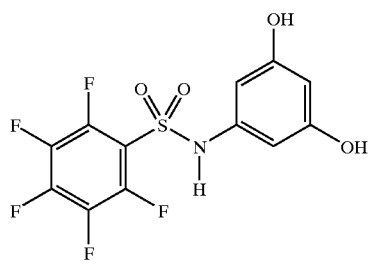

3,5-Dihydroxy-1-pentafluorophenylsulfonamidobenzene. $^1$H NMR (CDCl$_3$) 7.15 (s, 1H), 6.25 (s, 2H), 6.15 (s, 1H), 5.31 (s, 2H).

Example 30

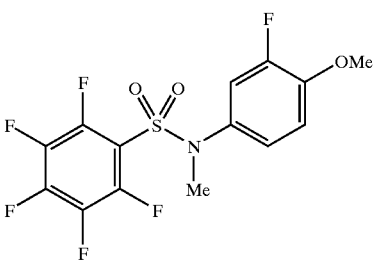

2-Fluoro-1-methoxy-4-(N-methylpentafluorophenylsulfonamido)benzene. Prepared using a procedure similar to that of Example 18 replacing 4-(N,N-dimethylamino)-1-pentafluorophenylsulfonamidobenzene with the appropriate non-substituted sulfonamide (product of Example 7). $^1$H NMR (CDCl$_3$): 6.97–6.94(m, 2H), 6.89(t, J=9 Hz, 1H), 3.87(s, 3H), 3.35ppm (t, J=1 Hz). EI m/z: 385(20, M$^+$), 154(100). Anal. calcd. for C$_{14}$H$_9$F$_6$NO$_3$: C, 43.64; H,2.35; N, 3.64. Found C, 43.55; H, 2.38; N, 3.65.

Example 31

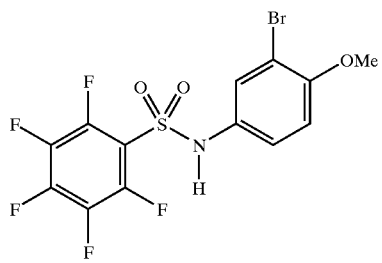

2-Bromo-1-methoxy4-pentafluorophenylsulfonamidobenzene. $^1$H NMR (CDCl$_3$): 7.35(d, J=3 Hz, 1H), 7.15(dd, J=9 Hz, 3 Hz, 1H), 6.97 (s, 1H), 6.81(d, J=9 Hz, 1H), 3.88 ppm (s, 3H). EI m/z: 433(35, M$^+$), 202(100). The compound was prepared by a protocol similar to that of example 1 by replacing N,N-dimethyl-1,4-phenyldiamine dihydrochloride with 3-bromo-4-methoxyaniline.

Example 32

2-Chloro-1-methoxy-4-pentafluorophenylsulfonamidobenzene. $^1$H NMR (CDCl$_3$): 7.19(d, J=3 Hz, 1H), 7.08(dd, J=9 Hz, 3 Hz, 1H), 7.01 (s, 1H), 6.84(d, J=9 Hz, 1H), 3.85 ppm (s, 3H). EI m/z (rel. abundance): 387(10, M$^+$), 156(100). The compound was prepared by a protocol similar to that of example 1 by replacing N,N-dimethyl-1,4-phenyldiamine dihydrochloride with 3-chloro-4-methoxyaniline.

Example 33

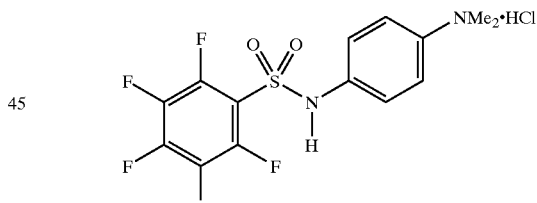

4-(N,N)-Dimethylamino)-1-pentafluorophenylsulfonamidobenzene hydrochloride.

4-(N,N-Dimethylamino)-1-pentafluorophenylsulfonamidobenzene (2 g, 5.5 mmol) was dissolved in 15 mL of diethyl ether at ambient temperature under nitrogen. Gaseous HCl was bubbled into the reaction mixture for 5 min. The mixture was filtered and the resulting solid washed twice with 15 mL portions of ice cold diethyl ether to afford the product as a white solid (1.89 g, 86% yield). $^1$H NMR (CD$_3$OD): 7.62(dd, J=9.0 Hz, 1.6 Hz, 2H), 7.44(dd, J=9.0 Hz, 1.6 Hz, 2H), 3.28 ppm (s, 6H). FAB m/z: 367(100%, M+H$^+$), 135(90%), 121(45%). Anal. calcd. for C$_{14}$H$_{13}$ClF$_5$N$_2$O$_2$S: C, 41.79; H, 3.01; N, 6.97; S, 7.95. Found C, 41.71; H, 3.05; N, 7.01; S, 7.96.

Example 34

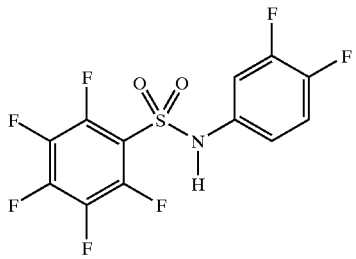

3,4-Difluoro-1-pentafluorophenylsulfonamidobenzene. The compound was prepared in a manner similar to that of example 1 by replacing N,N-dimethyl-1,4-phenyldiamine dihydrochloride with 3,4-difluoroaniline. $^1$H NMR (CDCl$_3$) 7.13 (m, 3H), 6.91 ppm (m, 1H). EI, m/z (relative abundance): 359 (20), 128 (100). Anal. calcd. for $C_{13}H_4F_7NO_2S$: C, 40.12; H, 1.12; N, 3.90. Found: C, 40.23; H, 1.17; N, 3.89.

Example 35

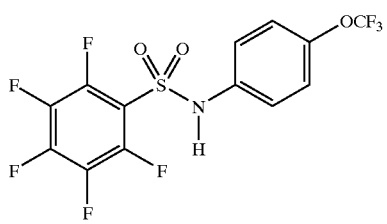

4-Trifluoromethoxy-1-pentafluorophenylsulfonamidobenzene. The compound was prepared in a manner similar to that of example 1 by replacing N,N-dimethyl-1,4-phenyldiamine dihydrochloride with 4-(trifluoromethoxy)aniline. $^1$H NMR (CDCl$_3$) 7.18 ppm (m, 4H). EI, m/z (relative abundance): 407 (20), 176 (100). Anal. calcd. for $C_{13}H_5F_8NO_3S$: C, 38.34; H, 1.24; N, 3.44. Found: C, 38.33; H, 1.30; N, 3.43.

Example 36

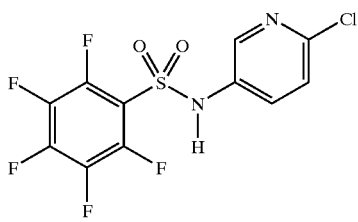

2-Chloro-5-pentafluorophenylsulfonamidopyridine. The compound was prepared in a manner similar to that of example 1 by replacing N,N-dimethyl-1,4-phenyldiamine dihydrochloride with 5-amino-2-chloropyridine. H NMR (DMSO-d$^6$): 8.18 (d, J=2.68 Hz, 1H), 7.64 (dd, J=8.75, 2.89 Hz, 1H), 7.50 ppm (d, J=8.75 Hz, 1H). EI m/z 358 (20, M$^+$), 127 (100). Anal. calcd. for $C_{11}H_4ClF_5N_2O_2S$: C, 36.83; H, 1.12; N, 7.81; S, 8.94; Cl, 9.90. Found: C, 37.00; H, 1.16; N, 7.78; S, 8.98; Cl, 10.01. White crystals with M.P.=144–145° C.

Example 37

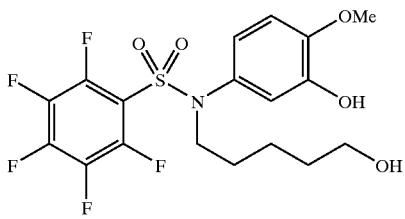

2-Hydroxy-1-methoxy-4-(N-(5-hydroxypentyl)-pentafluorophenylsulfonamido)benzene.

N-(5-hydroxypentyl)-2-hydroxy-1-methoxy-4-aminobenzene was prepared by reductive amination of 5-amino-2-methoxy phenol with glutaric dialdehyde with NaBH$_4$ in MeOH. 2-Hydroxy-1-methoxy-4-(N-(5-hydroxypentyl)-pentafluorophenylsulfonamido)benzene was prepared in a manner similar to that of example 1 by replacing N,N-dimethyl-1,4-phenyldiamine dihydrochloride with N-(5-hydroxypentyl)-2-hydroxy-1-methoxy-4-aminobenzene. $^1$H NMR (CDCl$_3$): 6.78(d, J=8.6 Hz, 1H), 6.71(dd, J=8.59, 2.48 Hz, 1H), 6.63(d, J=2.48 Hz, 1H), 3.88(s, 3H), 3.7(t, J=6.8 Hz, 2H), 3.6(t, J=6.39 Hz, 2H), 1.5 ppm (m, 6H). Anal. calcd. for $C_{18}H_{18}F_5NO_5S$: C, 47.47; H, 3.98; N, 3.08; S, 7.04. Found: C, 47.47; H, 4.04; N, 3.11; S, 6.97. White crystals with M.P.=118°.

Example 38

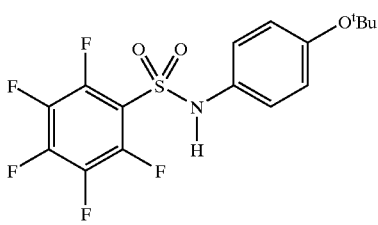

4-(1,1-Dimethyl)ethoxy-1-pentafluorophenylsulfonamidobenzene.

The compound was prepared in a manner similar to example 46 by replacing 3-chloroaniline with 4-t-butoxyaniline. 4-t-Butoxyaniline was prepared by the method of Day (*J. Med. Chem.* 1975, 18, 1065). $^1$H NMR (CDCl$_3$): d 7.07 (m, 2), 6.92 (m, 2), 6.88 (m, 1), 1.31 (s, 9). MS (EI): m/z 395 (1, M$^+$), 339 (28), 108 (100). Anal. Calcd. for $C_{16}H_{14}F_5NO_3S$: C, 48.61; H, 3.57; N, 3.54; S, 8.11. Found: C, 48.53; H, 3.60; N, 3.50; S, 8.02.

Example 39

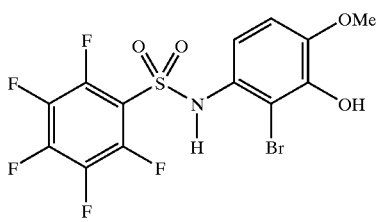

1-Bromo-3-hydroxy-4-methoxy-1-pentafluorophenylsulfonamidobenzene. The compound was prepared by bromination of the compound of example 6 with N-bromosuccinimide in dichloromethane. $^{1}$H NMR (CDCl$_3$) 7.28(br s, 1H), 7.21 (d, J=9 Hz, 1H), 6.80 (d, J=9 Hz, 1H), 6.05 (s, 1H), 3.89 ppm (s, 3H). EI, m/z (relative abundance): 449 (25), 447 (25), 218 (100), 216 (100). Anal. calcd. for C$_{13}$H$_8$BrF$_5$NO$_4$S: C, 34.84; H, 1.57; N, 3.13; S, 7.15. Found: C, 34.75; H, 1.60; N, 3.07; S, 7.08.

Example 40

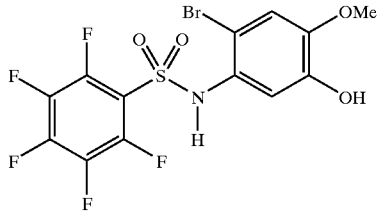

2-Bromo-4-methoxy-5-hydroxy-1-pentafluorophenylsulfonamidobenzene. The compound was prepared by bromination of the compound of example 6 with N-bromosuccinimide in dichloromethane. $^{1}$H NMR (CDCl$_3$) 7.28 (s, 1H), 7.16 (br s, 1H), 6.91 (s, 1H), 5.63 (s, 1H), 3.85 ppm (s, 3H). EI, m/z (relative abundance): 449 (25), 447 (25), 218 (100), 216 (100). Anal. calcd. for C$_{13}$H$_8$BrF$_5$NO$_4$S: C, 34.84; H, 1.57; N, 3.13; S, 7.15. Found: C, 34.84; H, 1.57; N, 3.05; S, 7.06.

Example 41

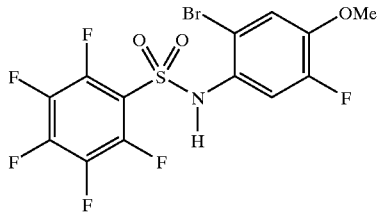

1-Bromo-4-fluoro-5-methoxy-2-pentafluorophenylsulfonamidobenzene. The compound was prepared by bromination of the compound of example 7 with bromine water. 1H NMR (CDCl$_3$): 7.49 (d, J=11.72 Hz, 1H), 7.21 (s, 1H), 7.04 (d, J=8.2 Hz, 1H), 3.84 ppm (s, 3H). EI m/z: 449 (20, M$^+$), 451 (20), 228 (100), 230 (100). Anal. Calcd. for C$_{13}$H$_6$BrF$_6$NO$_3$S: C, 34.69; H, 1.34; N, 3.11; S, 7.12; Br, 17.75. Found: C, 34.76; H, 1.29; N, 3.05; S, 7.12; Br, 17.68. White crystals with M.P.=109° C.

Example 42

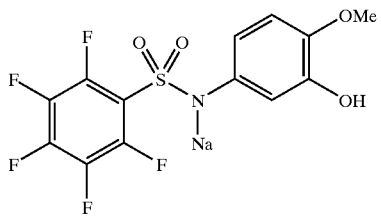

2-Hydroxy-1-methoxy-4-pentafluorophenylsulfonamidobenzene sodium salt. The compound was prepared by treating the compound of example 6 with an equimolar amount of 1N NaOH$_{(aq)}$. The mixture was then lyophilized and the residue recrystallyzed from ethyl acetate/ether. $^{1}$H NMR (DMSO) 8.40 (s, 1H), 6.57 (d, J=9 Hz, 1H), 6.39 (d, J=2 Hz, 1H), 6.24 (dd, J=9, 2 Hz, 1H), 3.62 ppm (s, 3H). Anal. calcd. for C$_3$H$_7$F$_5$NNaO$_4$S: C, 39.91; H, 1.80; N, 3.58; Na, 5.88; S, 8.19. Found: C, 39.79; H, 1.86; N, 3.50; Na, 5.78; S, 8.07.

Example 43

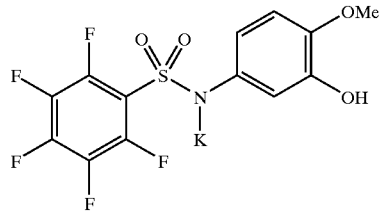

2-Hydroxy-1-methoxy-4-pentafluorophenylsulfonamidobenzene potassium salt. The compound was prepared in a manner similar to that of example 42 by replacing 1N NaOH with 1N KOH. $^{1}$H NMR (DMSO) 8.30 (br s, 1H), 6.55 (d, J=9 Hz, 1H), 6.36 (d, J=2 Hz, 1H), 6.25 (dd, J=9, 2 Hz, 1H), 3.61 ppm (s, 3H). Anal. calcd. for C$_{13}$H$_7$F$_5$KNO$_4$S: C, 38.33; H, 1.73; N, 3.44; S, 7.87. Found: C, 38.09; H, 1.79; N, 3.39; S, 7.97.

Example 44

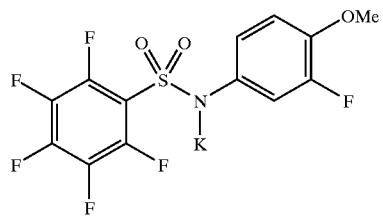

2-Fluoro-1-methoxy-4-pentafluorophenylsulfonamidobenzene potassium salt. The compound was prepared in a manner similar to that of example 43 by replacing the compound from example 6 with example 7. $^{1}$H NMR (DMSO) 6.80 (t, J=10 Hz, 1H), 6.72 (dd, J=9, 2 Hz, 1H), 6.54 (dd, J=9, 2 Hz, 1H), 3.68 ppm (s, 3H). Anal. calcd. for C$_{13}$H$_6$F$_6$KNO$_3$S: C, 38.15; H, 1.48; N, 3.42; S, 7.83. Found: C, 38.09; H, 1.51; N, 3.35; S, 7.73. M.P.=202–205° C.

Example 45

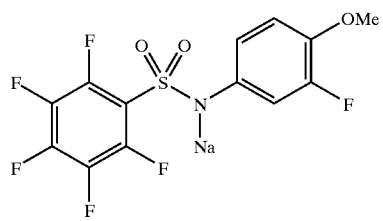

2-Fluoro-1-methoxy-4-pentafluorophenylsulfonamidobenzene sodium salt. The compound was prepared in a manner similar to that of example 44 by replacing 1N KOH with 1N NaOH. $^{1}$H NMR (DMSO) 6.80 (t, J=10 Hz, 1H), 6.71 (dd, J=9, 2 Hz, 1H),

Example 46

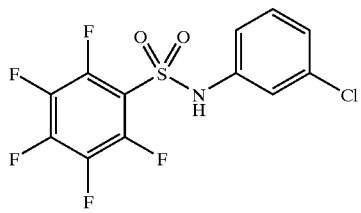

3-Chloro-1-pentafluorophenylsulfonamidobenzene. To a solution of pentafluorophenylsulfonyl chloride (0.15 mL, 1.00 mmol) in MeOH (4 mL) was added 3-chloroaniline (260 mg, 2.04 mmol). After stirring at rt for 1 h, the reaction mixture was concentrated under reduced pressure and the residue was taken up in EtOAc and then filtered through a plug of silica gel. The filtrate was concentrated to give a yellow oil that upon chromatography provided 265 mg (74%) of product. $^1$H NMR (CDCl$_3$): d 7.28–7.24 (m, 1H), 7.21–7.17 (m, 2H), 7.10–7.08 (m, 1H), 7.07 (s, 1H). MS (EI): m/z 357 (42, M$^+$), 258 (76), 126 (87), 99 (100). Anal. Calcd. for C$_{12}$H$_5$ClF$_5$NO$_2$S: C, 40.30; H, 1.41; N, 3.92; S, 8.96. Found: C, 40.18; H, 1.35; N, 3.84; S, 8.90.

Example 47

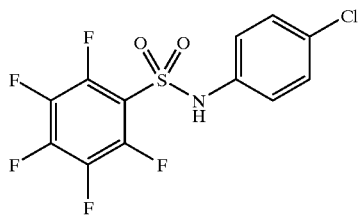

4-Chloro-1-pentafluorophenylsulfonamidobenzene. The compound was prepared in a manner similar to that described in example 46 by replacing 3-chloroaniline with 4-chloroaniline. $^1$H NMR (CDCl$_3$): d 7.30 (m, 2H), 7.20 (m, 1H), 7.14 (m, 2H). MS (EI): m/z 357 (27, M$^+$), 258 (38), 126 (100), 99 (85). Anal. Calcd. for C$_{12}$H$_5$ClF$_5$NO$_2$S: C, 40.30; H, 1.41; N, 3.92; S, 8.96. Found: C, 40.19; H, 1.37; N, 3.87; S, 8.88.

Example 48

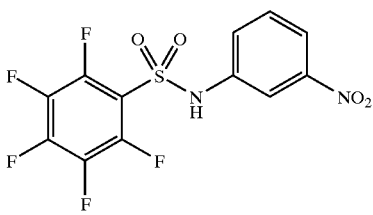

3-Nitro-1-pentafluorophenylsulfonamidobenzene. The compound was prepared in a manner similar to that described in example 46 by replacing 3-chloroaniline with 3-nitroaniline. 1H NMR (CDCl$_3$): d 8.14 (s, 1H), 8.06–8.03 (m, 2H), 7.66–7.63 (m, 1H), 7.55 (m, 1H). MS (EI): m/z 368 (54, M$^+$), 137 (70), 91 (100). Anal. Calcd. for C$_{12}$H$_5$F$_5$N$_2$O$_4$S: C, 39.14; H, 1.37; N, 7.61; S, 8.71. Found: C, 39.39; H, 1.45; N, 7.46; S, 8.58.

Example 49

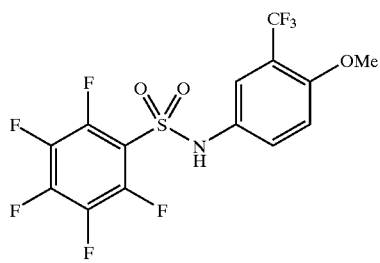

4-Methoxy-1-pentafluorophenylsulfonamido-3-trifluoromethylbenzene. The compound was prepared in a manner similar to that described in example 46 by replacing 3-chloroaniline with 4-methoxy-3-trifluoromethylaniline which was obtained by the hydrogenation of the corresponding nitro compound. White solid, mp 121–123° C. $^1$H NMR (CDCl$_3$): d 7.43–7.37 (m, 2H), 6.96 (d, J=8.8, 1H), 3.88 (s, 3H). MS (EI): m/z 421 (16, M$^+$), 190 (100). Anal. Calcd. for C$_{14}$H$_7$F$_8$NO$_3$S: C, 39.92; H, 1.67; N, 3.32; S, 7.61. Found: C, 40.17; H, 1.68; N, 3.28; S, 7.67.

Example 50

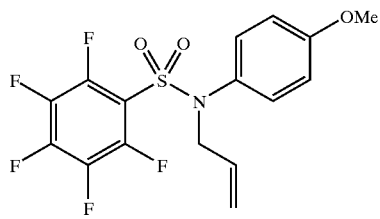

4-Methoxy-1-(N-(2-propenyl)pentafluorophenylsulfonamido)benzene. To a solution of 4-methoxy-1-pentafluorophenylsulfonamidobenzene (448 mg, 1.27 mmol) in THF (3 mL) was added triphenylphosphine (333 mg, 1.27 mmol) and allyl alcohol (0.09 mL, 1.27 mmol). Diethylazodicarboxylate (0.20 mL, 1.27 mmol) was added and the mixture was stirred at rt. After 1 h, the reaction mixture was poured onto saturated NaCl (10 mL) and extracted with CH$_2$Cl$_2$ (3×10 mL). The combined organic extracts were washed with saturated NaHCO$_3$ (10 mL) and dried (MgSO$_4$). Concentration followed by flash chromatography (25:25:1/hexanes:CH$_2$Cl$_2$:EtOAc) provided 451 mg (90%) of product as a white solid, mp 59–60° C. $^1$H NMR (CDCl$_3$): d 7.06 (m, 2H), 6.85 (m, 2H), 5.79 (m, 1H), 5.15 (s, 1H), 5.11 (m, 1H), 4.37 (d, J=6.3, 2H), 3.80 (s, 3H). MS (EI): m/z 393 (33, M$^+$), 162 (100), 134 (66). Anal. Calcd. for C$_{16}$H$_{11}$F$_5$NO$_3$S: C, 48.98; H, 2.83; N, 3.57; S, 8.17. Found: C, 49.13; H, 3.15; N, 3.63; S, 8.15.

Example 51

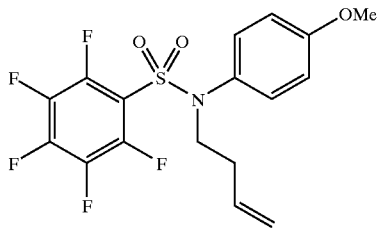

1-(N-(3-Butenyl)pentafluorophenylsulfonamido)-4-methoxybenzene. The compound was prepared in a manner similar to that described in example 50 by replacing allyl alcohol with 3-buten-1-ol. White solid, mp 64–66° C. $^1$H NMR (CDCl$_3$): d 7.08 (m, 2H), 6.86 (m, 2H), 5.74 (m, 1H), 5.10–5.04 (m, 2H), 3.83 (m, 2H), 3.81 (s, 3H), 2.25 (q, J=6.9, 2H). MS (EI): m/z 407 (13, M$^+$), 366 (24), 135 (100). Anal. Calcd. for C$_{17}$H$_{14}$F$_5$NO$_3$S: C, 50.13; H, 3.46; N, 3.44; S, 7.87. Found: C, 50.25; H, 3.51; N, 3.43; S, 7.81.

Example 52

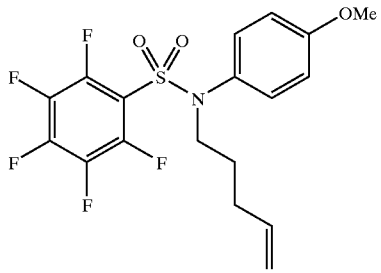

4-Methoxy-1-(N-(4-pentenyl)pentafluorophenylsulfonamido)benzene. The compound was prepared in a manner similar to that described in example 50 by replacing allyl alcohol with 4-penten-1-ol. Low melting semi-solid. $^1$H NMR (CDCl$_3$): d 7.08 (m, 2H), 6.87 (m, 2H), 5.74 (m, 1H), 5.02–4.96 (m, 2H), 3.81 (s, 3H), 3.76 (t, J=7.04, 2H), 2.11 (q, J=6.9, 2H), 1.60 (pentet, J=7.3, 2H). MS (EI): m/z 421 (30, M$^+$), 190 (100). Anal. Calcd. for C$_{18}$H$_{16}$F$_5$NO$_3$S: C, 51.31; H, 3.83; N, 3.32; S, 7.61. Found: C, 51.44; H, 3.89; N, 3.38; S, 7.54.

Example 53

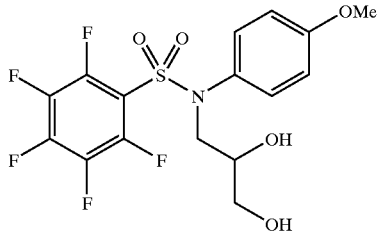

1-(N-(2,3-Dihydroxypropyl)pentafluorophenylsulfonamido)-4-methoxybenzene. To a solution of 4-methoxy-1-(N-(2-propenyl)pentafluorophenylsulfonamido)benzene (101 mg, 0.26 mmol) in acetone:water (8:1, 1 mL) at rt was added N-methylmorpholine N-oxide (34.0 mg, 0.29 mmol) and OsO$_4$ (0.10 mL of 0.16 M solution in H$_2$O, 1.60×10$^{-2}$ mmol). After stirring at rt for 18 h, the reaction mixture was treated with saturated NaHSO$_3$ (5 mL) and allowed to stir at rt. After 1 h, the reaction mixture was poured onto saturated NaHSO$_3$ (5 mL) and extracted with CH$_2$Cl$_2$ (3×10 mL). The combined organic extracts were dried (MgSO$_4$) and concentrated. Flash chromatography (1:1, 1:2/hexanes:EtOAc) afforded 90 mg (83%) of product as a white solid, mp 130–131° C. $^1$H NMR (CDCl$_3$): d 7.11 (m, 2H), 6.85 (m, 2H), 3.78 (s, 3H), 3.90–3.65 (m, 5H). Anal. Calcd. for C$_{16}$H$_{13}$F$_5$NO$_5$S: C, 45.08; H, 3.07; N, 3.29; S, 7.52. Found: C, 45.09; H, 3.33; N, 3.27; S, 7.46.

Example 54

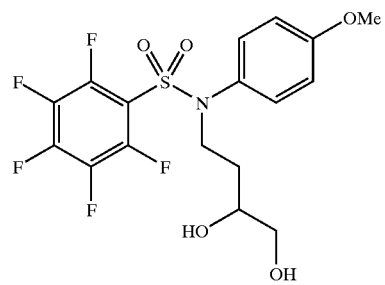

1-(N-(3,4-Dihydroxybutyl)pentafluorophenylsulfonamido)-4-methoxybenzene. The compound was prepared in a manner similar to that described in example 53 by replacing 4-methoxy-1-(N-(2-propenyl)pentafluorophenylsulfonamido)benzene with 1-(N-(3-butenyl)pentafluorophenylsulfonamido)-4-methoxybenzene. White solid, mp 126–128° C. $^1$H NMR (CDCl$_3$): d 7.10 (m, 2H), 6.88 (m, 2H), 4.13 (m, 1H), 3.96 (m, 1H), 3.81 (s, 3H), 3.78–3.73 (m, 1H), 3.64 (dd, 1, J=2.9, 10.7, 1H), 3.47 (dd, J=7.3, 11.2; 1H), 2.67 (bs, 1H), 1.92 (bs, 1H), 1.62 (m, 2H).

Example 55

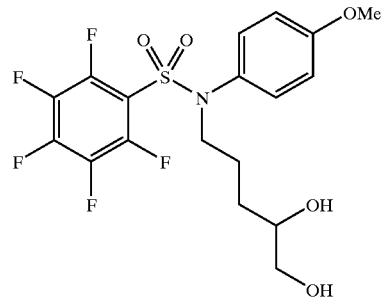

1-(N-(4,5-Dihydroxypentyl)pentafluorophenylsulfonamido)-4-methoxybenzene. The compound was prepared in a manner similar to that described in example 53 by replacing 4-methoxy-1-(N-(2-propenyl)pentafluorophenylsulfonamido)benzene with 4-methoxy-1-(N-(4-pentenyl)pentafluorophenylsulfonamido)benzene. White solid, mp 116–118° C. $^1$H NMR (CDCl$_3$): d 7.07 (m, 2H), 6.86 (m, 2H), 3.80 (s, 3H), 3.78 (m, 2H), 3.71–3.62 (m, 2H), 3.43 (dd, J=7.5, 10.8; 1H), 1.90 (bs, 2H), 1.66–1.49 (m, 4H). Anal. Calcd. for C$_{18}$H$_{18}$F$_5$NO$_5$S: C, 47.48; H, 3.98; N, 3.08; S, 7.04. Found: C, 47.58; H, 3.95; N, 3.06; S, 6.95.

Example 56

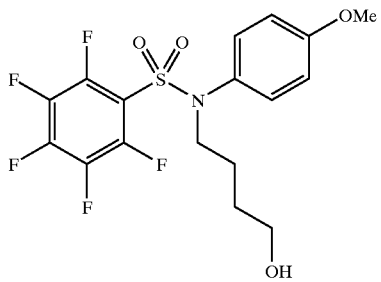

1-(N-(4-hydroxybutyl)pentafluorophenylsulfonamido)-4-methoxybenzene. To a solution of 1-(N-(3-butenyl)pentafluorophenylsulfonamido)-4-methoxybenzene (410 mg, 1.01 mmol) in THF (6.5 mL) at −78° C. was added BH$_3$·THF (1.00 mL of a 1 M solution in THF, 1.00 mmol). After stirring at −78° C. for 1 h and at 0° C. for 1 h, the reaction mixture was treated with H$_2$O (20 mL) and sodium perborate (513 mg, 5.14 mmol). After stirring at rt for 2 h, the mixture was poured onto H$_2$O (20 mL) and extracted with CH$_2$Cl$_2$ (3×15 mL). The combined organic extracts were washed with sat. NaCl (20 mL) and dried (MgSO$_4$). Concentration followed by chromatography (2:1/hexanes:EtOAc) afforded 270 mg (64%) of product as a white solid, mp 88–90° C. $^1$H NMR (CDCl$_3$): d 7.08 (m, 2H), 6.85 (m, 2H), 3.80 (s, 3H), 3.77 (m, 2H), 3.64 (t, J=6.0; 2H), 1.63–1.55 (m, 5H), 1.50 (bs, 1H). Anal. Calcd. for C$_{17}$H$_{16}$F$_5$NO$_4$S: C, 48.00; H, 3.79; N, 3.29; S, 7.54. Found: C, 48.08; H, 3.76; N, 3.34; S, 7.46.

Example 57

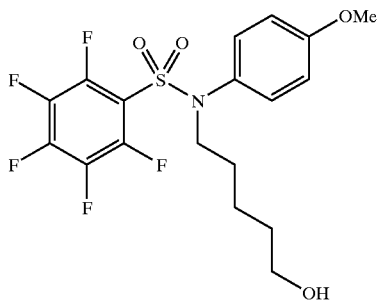

4-Methoxy-1-(N-(5-hydroxypentyl)pentafluorophenylsulfonamido)benzene. The compound was prepared in a manner similar to that described in example 56 by replacing 1-(N-(3-butenyl)pentafluorophenylsulfonamido)-4-methoxybenzene with 4-methoxy-1-(N-(4-pentenyl)pentafluorophenylsulfonamido)benzene. White solid, mp 96–97° C. $^1$H NMR (CDCl$_3$): d 7.08 (m, 2H), 6.86 (m, 2H), 3.81 (s, 3H), 3.76 (t, J=6.8, 2H), 3.62 (t, J=6.4; 2H), 1.58–1.43 (m, 6H). Anal. Calcd. for C$_{18}$H$_{18}$F$_5$NO$_4$S: C, 49.20; H, 4.13; N, 3.19; S, 7.30. Found: C, 49.11; H, 4.09; N, 3.14; S, 7.19.

Example 58

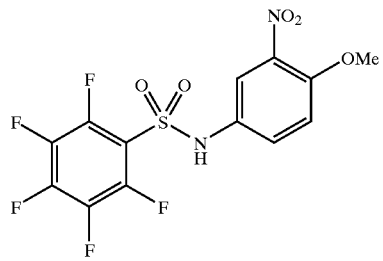

4-Methoxy-3-nitro-1-pentafluorophenylsulfonamidobenzene. The compound was prepared in a manner similar to example 46 by replacing 3-chloroaniline with 4-methoxy-3-nitroaniline which was prepared by the method of Norris (Aust. J. Chem. 1971, 24, 1449). Orange-yellow solid, mp 95–97° C. $^1$H NMR (CDCl$_3$): d 7.64 (d, J=2.7; 1H), 7.51 (dd, J=2.7, 9.0; 1H), 7.09 (s, 1H), 7.09 (d, J=9.0; 1H), 3.95 (s, 3H). Anal. Calcd. For C$_{13}$H$_7$F$_5$N$_2$O$_5$S: C, 39.21; H, 1.77; N, 7.03; S, 8.05. Found: C, 39.19; H, 1.73; N, 6.97; S, 7.95.

Example 59

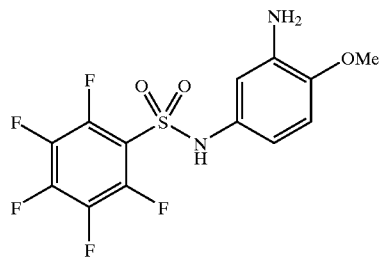

3-Amino-4-methoxy-1-pentafluorophenylsulfonamidobenzene. To a solution of 4-methoxy-3-nitro-1-pentafluorophenylsulfonamidobenzene (627 mg, 1.58 mmol) in ethanol (10 mL) was added 10% Pd/C (51 mg). The resulting mixture was stirred under an atmosphere of hydrogen gas at 1 atm pressure. After 14 h, the mixture was passed through a pad of celite and the filtrate was concentrated to give a solid residue. Silica gel chromatography (2:1, 1:1/hexanes:EtOAc) yielded 542 mg (93%) of product as a white solid, mp 142–143° C. $^1$H NMR (DMSO-d$_6$): 10.64 (s, 1), 6.68 (d, J=8.4; 1H), 6.44 (d, J=2.1; 1H), 6.30 (d, J=2.1, 8.4; 1H), 4.88 (bs, 2H), 3.69 (s, 3H). Anal. Calcd. for C$_{13}$H$_9$F$_5$N$_2$O$_3$S: C, 42.40; H, 2.46; N, 7.61; S, 8.71. Found: C, 42.29; H, 2.36; N, 7.52; S, 8.60.

Example 60

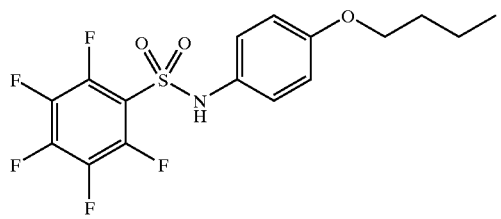

4-Butoxy-1-pentafluorophenylsulfonamidobenzene. To a solution of pentafluorophenylsulfonyl chloride (203 mg, 0.763 mmol) in MeOH (4 mL) was added 4-butoxyaniline (0.26 mL, 1.53 mmol). After stirring at rt for 1 h, the reaction mixture was poured onto 1 MHCl (15 mL) and extracted with CH$_2$Cl$_2$ (3×10 mL). The combined organic extracts were washed with saturated NaCl (10 mL) and dried (MgSO$_4$). Concentration followed by flash chromatography (25:25:1/hexanes: CH$_2$Cl$_2$:EtOAc) provided 189 mg (63%) of product. $^1$H NMR (CDCl$_3$): d 7.07 (m, 2H), 6.86 (s, 1H), 6.80 (m, 2H), 3.89 (t, J=6.5; 2H), 1.73 (m, 2H), 1.46 (m, 2H), 0.95 (t, J=7.5; 2H). MS (EI): m/z 395 (30, M$^+$), 164 (35), 108 (100). Anal. Calcd. for C$_{16}$H$_{14}$F$_5$NO$_3$S: C, 48.61; H, 3.57; N, 3.54; S, 8.11. Found: C, 48.54; H, 3.53; N, 3.50; S, 8.02.

Example 61

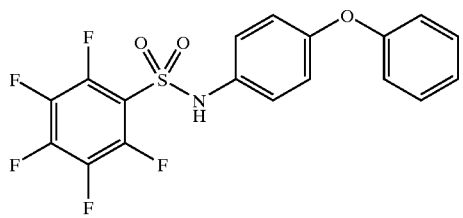

1-Pentafluorophenylsulfonamido-4-phenoxybenzene. The compound was prepared in a manner similar to that described in example 60 by replacing 4-butoxyaniline with 4-phenoxyaniline. $^1$H NMR (CDCl$_3$): 7.36–7.30 (m, 2H), 7.15–7.10 (m, 3H), 6.99 (s, 1H), 6.98–6.90 (m, 4H). MS (EI): m/z 415 (32, M$^+$), 184 (100), 77 (66). Anal. Calcd. for C$_{18}$H$_{10}$F$_5$NO$_3$S: C, 52.05; H, 2.43; N, 3.27; S, 7.72. Found: C, 51.78; H, 2.45; N, 3.25; S, 7.53.

Example 62

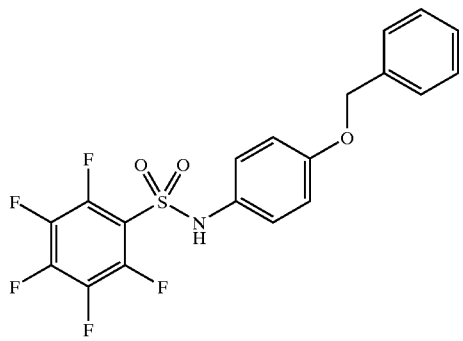

4-Benzyloxy-1-pentafluorophenylsulfonamidobenzene. The compound was prepared in a manner similar to that described in example 60 by replacing 4-butoxyaniline with 4-benzyloxyaniline. 4-Benzyloxyaniline was obtained from the commercially available hydrochloride salt by treatment with aqueous NaOH. $^1$H NMR (CDCl$_3$): 7.38–7.37 (m, 4H), 7.36–7.32 (m, 1H), 7.10–7.08 (m, 2H), 7.91–7.88 (m, 2H), 6.78 (s, 1H), 5.01 (s, 1H). MS (EI): m/z 429 (19, M), 91 (100). Anal. Calcd. for C$_{19}$H$_{12}$F$_5$NO$_3$S: C, 53.14; H, 2.82; N, 3.26; S, 7.45. Found: C, 53.07; H, 2.78; N, 3.21; S, 7.35.

Example 63

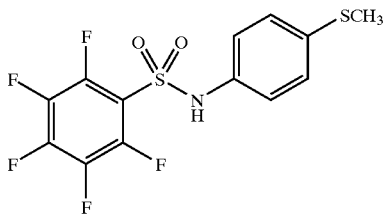

4-Methylmercapto-1-pentafluorophenylsulfonamidobenzene. The compound was prepared in a manner similar to that described in example 60 by replacing 4-butoxyaniline with 4-(methylmercapto) aniline. $^1$H NMR (CDCl$_3$): 7.17 (m, 2H), 7.09 (m, 2H), 6.89 (m, 1H), 2.44 (s, 3H). MS (EI): m/z 369 (24, M$^+$), 138 (100), 77 (66). Anal. Calcd. for C$_{13}$H$_8$F$_5$NO$_2$S$_2$: C, 42.28; H, 2.18; N, 3.79; S, 17.36. Found: C, 42.20; H, 2.21; N, 3.72; S, 17.28.

Example 64

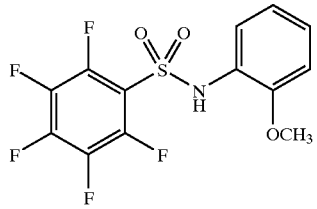

2-Methoxy-1-pentafluorophenylsulfonamidobenzene. The compound was prepared in a manner similar to that described in example 60 by replacing 4-butoxyaniline with o-anisidine. $^1$H NMR (CDCl$_3$): d 7.54 (dd, J=1.5, 8.0; 1H), 7.13 (dt, J=1.5, 8.0; 1H), 6.94 (dt, J=1.2, 8.0; 1H), 6.84 (dd, J=1.2, 8.0; 1H), 3.79 (s, 3H). MS (EI): m/z 353 (82, M$^+$), 122 (100), 94 (95). Anal. Calcd. for C$_{13}$H$_8$F$_5$NO$_3$S: C, 44.19; H, 2.28; N, 3.97; S, 9.06. Found: C, 44.10; H, 2.26; N, 3.92; S, 9.03.

Example 65

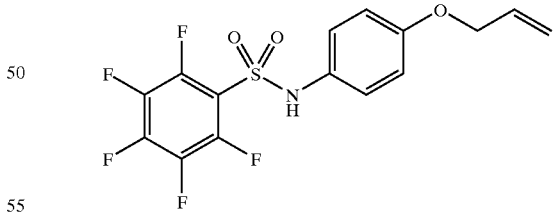

4-Allyloxy-1-pentafluorophenylsulfonamidobenzene. The compound was prepared in manner similar to that described in example 60 by replacing 4-butoxyaniline with 4-allyloxyaniline. 4-Allyloxyaniline was prepared by the method of Butera (J. Med. Chem. 1991, 34, 3212). $^1$H NMR (CDCl$_3$): 7.08 (m, 2H), 6.87 (m, 1H), 6.82 (m, 2H), 6.04–5.94 (m, 1H), 5.39–5.34 (m, 1H), 5.29–5.25 (m, 1H), 4.48–4.46 (m, 2H). MS (EI): m/z 379 (11, M$^+$), 148 (32), 41 (100). Anal. Calcd. for C$_{15}$H$_{10}$F$_5$NO$_3$S: C, 47.50; H, 2.66; N, 3.96; S, 8.45. Found: C, 47.53; H, 2.68; N, 3.62; S, 8.37.

Example 66

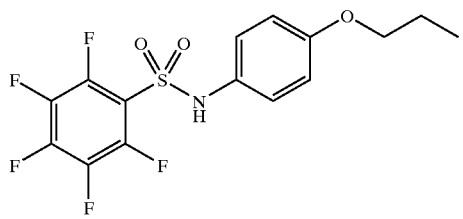

1-Pentafluorophenylsulfonamido-4-propoxybenzene. The compound was prepared in a manner similar to that described in example 60 by replacing 4-butoxyaniline with 4-propoxyaniline. 4-Propoxyaniline was obtained by catalytic hydrogenation of 4-allyloxynitrobenzene. 4-Allyloxynitrobenzene was prepared by the method of Butera (*J. Med. Chem.* 1991, 34, 3212). $^1$H NMR (CDCl$_3$): 7.09 (m, 2H), 6.82 (m, 2H), 6.78 (m, 1H), 3.87 (t, J=6.5; 2H), 1.78 (m, 2H), 1.02 (t, J=7.4; 3H). MS (EI): m/z 381 (20, M$^+$), 150 (40), 108 (100). Anal. Calcd. for C$_{15}$H$_{12}$F$_5$NO$_3$S: C, 47.25; H, 3.17; N, 3.67; S, 8.41. Found: C, 47.01; H, 3.20; N, 3.61; S, 8.31.

Example 67

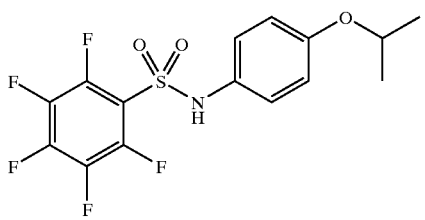

4-(1-Methyl)ethoxy-1-pentafluorophenylsulfonamidobenzene. The compound was prepared in a manner similar to that described in example 60 by replacing 4-butoxyaniline with 4-isopropoxyaniline. 4-Isopropoxyaniline was prepared from 4-fluoronitrobenzene in analogy to the method of Day (*J. Med. Chem.* 1975, 18, 1065). $^1$H NMR (CDCl$_3$): 7.08 (m, 2H), 7.00 (s, 1H), 6.81 (m, 2H), 4.48 (heptet, J=6.1; 1H), 1.30 (d, J=6.04; 6H). MS (EI): m/z 381(7, M$^+$), 339 (8), 108 (100). Anal. Calcd. for C$_{15}$H$_{12}$F$_5$NO$_3$S: C, 47.25; H, 3.17; N, 3.67; S, 8.41. Found: C, 47.08; H, 3.18; N, 3.60; S, 8.34.

Example 68

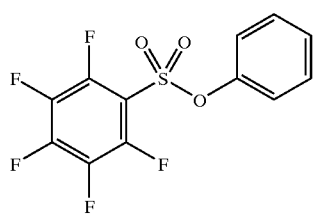

1-Pentafluorophenylsulfonyloxybenzene. To a stirred solution of phenol (0.068 g, 0.729 mmol) in dimethylformamide (3.65 mL) at 25° C. is added pentafluorophenyl sulfonyl chloride (0.135 mL, 0.911 mmol), followed by sodium carbonate (0.116 g, 1.09 mmol), and the reaction mixture is stirred for 18 hours. The reaction mixture is diluted with ethyl acetate (50 mL), washed with 20% ammonium chloride (2×20 mL), and saturated sodium chloride (2×20 mL). The organic layer is dried (sodium sulfite), and the ethyl acetate removed under vacuum. Column chromatography (3/1 ethyl acetate/hexane) yields the title compound.

Example 69

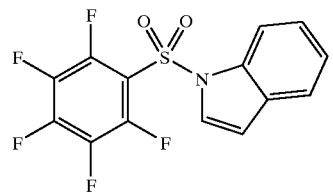

1-Pentafluorophenylsulfonylindole. To a stirred solution of indole (0.085 g, 0.729 mmol) in dimethylformamide (3.65 mL) at 25° C. is added pentafluorophenyl sulfonyl chloride (0.135 mL, 0.911 mmol), followed by sodium carbonate (0.116 g, 1.09 mmol), and the reaction mixture is stirred for 18 hours. The reaction mixture is diluted with ethyl acetate (50 mL), washed with 20% ammonium chloride (2×20 mL), and saturated sodium chloride (2×20 mL). The organic layer is dried (sodium sulfite), and the ethyl acetate removed under vacuum. Column chromatography (3/1 ethyl acetate/hexane) yields the title compound.

Example 70

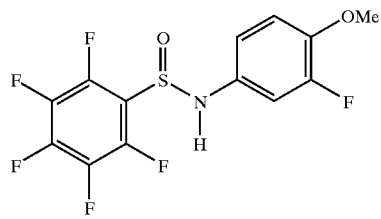

2-Fluoro-1-methoxy-4-pentafluorophenylsulfinamidobenzene. To 3-fluoro-p-anisidine (3 g, 21.2 mmol) suspended in THF (50 mL) with pyridine (1.84 g, 23.3 mmol) at 0° C. under argon is added dropwise pentafluorophenylsulfinyl chloride (5.3 g, 21.2 mmol). The reaction mixture is stirred for 30 min. at 0° C. and allowed to warm to ambient temperature. The reaction mixture is stirrred at room temperature and followed by TLC. After the reaction is completed the mixture is diluted with ethyl acetate and the reaction quenched with water. The layers are separated and the aqueous layer extracted twice with ethyl acetate. The organic layers are combined and dried with brine and with Na$_2$SO$_4$. The solvent is evaporated and the residue purified by chromatography on silica to give the title compound.

Example 71

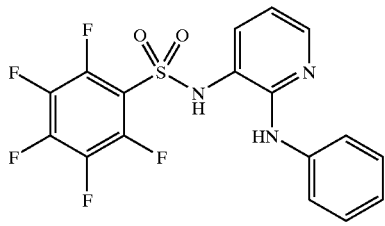

2-Anilino-3-pentafluorophenylsulfonamidopyridine. To a solution of pentafluorophenylsulfonyl chloride (863 mg, 3.24 mmol) in pyridine (9 mL) at rt was added 3-amino-2-analinopyridine (600 mg, 3.24 mmol). After stirring at rt overnight the reaction mixture was concentrated at reduced pressure and the residue partitioned between 1 M Hcl (50 mL) and CH2Cl2 (50 mL). The organic extract was dried and concentrated to give an oil which was purified by MPLC to give 377 mg (28%) of product as an orange solid. $H^1$ NMR (CDCl$_3$): 8.50 (bs, 1H), 7.80 (d, J=5.1, 1H), 7.61 (d, J=8.0, 1H), 7.32 (t, J=8.0, 2H), 7.25 (d, J=8.0, 2H), 7.11 (t, J=7.3, 1H), 6.80 (dd, J=5.6, 7.7, 1H), 4.20 (bs, 1H). MS (FAB): m/z 438 (M+Na), 416 (M+H).

Example 72

4-[3H]-1-Fluoro-2-methoxy-5-pentafluorosulfonamidobenzene.

A solution of 1-bromo-4-fluoro-5-methoxy-2-pentafluorophenylsulfonamidobenzene (27.8 mg, 0.058 mmol; prepared in Example 41) in ethyl acetate (2 mL) was treated with 100 mg of 10% palladium on charcoal. The air in the reaction vessel was evacuated and replaced with tritium gas. After 2 h of stirring at room temperature, the catalyst was filtered, the solvent was evaporated, and the crude product purified by preparative thin layer chromatography (TLC) using dichloromethane as the eluent. The sample purity was characterized by HPLC using a Microsorb silica (250×4.6 mm) 5 mm column and 15% ethyl acetate/hexane as the mobile phase. The elution of material was detected using a UV detector at 254 nm and a Beta Ram detector. The chemical purity of this material was determined to be 100%, and the radiochemical purity was 99.3%. The specific activity of this material was Ci/mmol.

Example 73

Compounds were evaluated for their ability to inhibit in vitro the growth of HeLa cells, an immortal cell line derived from a human cervical carcinoma commonly used to evaluate the cytotoxicity of potential therapeutic agents. The following data reflect the cytotoxicity of selected examples of the present invention. The values given represent the concentration of test compound required to inhibit by 50% the uptake of Alamar Blue (Biosource International, Camarillo, Calif.) by HeLa cell cultures, which correlates directly with the overall levels of cellular metabolism in the culture, and is generally accepted as an appropriate marker of cell growth. The test was conducted according to the method of S. A. Ahmed et al. (1994) J. Immunol. Methods 170: 211–224. The following selected examples display potent cytotoxic activity in this assay, with $IC_{50}$ values ranging from less than 0.05 µM to 10 µM.

| Compound | IC50 (µM) |
| --- | --- |
| Example 1 | <0.05 |
| Example 2 | 0.15 |
| Example 3 | 1.5 |
| Example 4 | 10 |
| Example 6 | <0.05 |
| Example 7 | <0.05 |
| Example 8 | <0.05 |
| Example 9 | 1 |
| Example 12 | 0.15 |
| Example 15 | 1 |
| Example 17 | 10 |
| Example 25 | 10 |
| Example 30 | 1.5 |
| Example 31 | 0.5 |
| Example 32 | 0.1 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating cancer or a cancerous condition, said method comprising administering to a mammalian subject in need thereof a therapeutically effective amount of a composition containing a compound of Formula I:

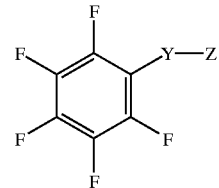

I wherein:
Y is —S(O)$_2$—;
Z is (i) a substituent of the formula NR$^1$R$^2$,
wherein R$^1$ and R$^2$ are independently selected from
substituted or unsubstituted (C1–C10)alkyl,
substituted or unsubstituted (C1–C10)alkoxyl,
substituted or unsubstituted (C3–C6)alkenyl,
substituted or unsubstituted (C2–C6)heteroalkyl,
substituted or unsubstituted (C3–C6)heteroalkenyl,
substituted or unsubstituted (C3–C6)alkynyl,
substituted or unsubstituted (C3–C8)cycloalkyl,
substituted or unsubstituted (C5–C7)cycloalkenyl,
substituted or unsubstituted (C5–C7)cycloalkadienyl,
substituted or unsubstituted aryl,
substituted or unsubstituted aryloxy,
substituted or unsubstituted aryl-(C3–C8)cycloalkyl,
substituted or unsubstituted aryl-(C5–C7)cycloalkenyl,
substituted or unsubstituted aryloxy-(C3–C8) cycloalkyl,
substituted or unsubstituted aryl-(C1–C4)alkyl,
substituted or unsubstituted aryl-(C1–C4)alkoxy,
substituted or unsubstituted aryl-(C1–C4)heteroalkyl, substituted or unsubstituted aryl-(C3–C6)alkenyl,
substituted or unsubstituted aryloxy-(C1–C4)alkyl,
substituted or unsubstituted aryloxy-(C2–C4) heteroalkyl,
substituted or unsubstituted heteroaryl,
substituted or unsubstituted heteroaryloxy,
substituted or unsubstituted heteroaryl-(C1–C4)alkyl,
substituted or unsubstituted heteroaryl-(C1–C4)alkoxy,
substituted or unsubstituted heteroaryl-(C1–C4) heteroalkyl,
substituted or unsubstituted heteroaryl-(C3–C6) alkenyl,
substituted or unsubstituted heteroaryloxy-(C1–C4) alkyl, and
substituted or unsubstituted heteroaryloxy-(C2–C4) heteroalkyl, and
wherein $NR^1R^2$ are further connected by a linking group E to give a substituent of the formula

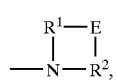

wherein E represents a bond, (C1–C4) alkylene, or (C1–C4) heteroalkylene, and the ring formed by $R^1$, E, $R^2$ and the nitrogen contains no more than 8 atoms;
or (ii) a substituent of formula —$NR^aR^b$ wherein $R^a$ is H and $R^b$ is selected from the group consisting of
substituted or unsubstituted heteroaryl,
substituted or unsubstituted heteroaryl-(C1–C4)alkyl,
substituted or unsubstituted heteroaryl-(C1–C4)alkoxy,
substituted or unsubstituted heteroaryl-(C1–C4) heteroalkyl,
substituted or unsubstituted heteroaryl-(C3–C6) alkenyl,
substituted or unsubstituted heteroaryloxy-(C1–C4) alkyl, and
substituted or unsubstituted heteroaryloxy-(C2–C4) heteroalkyl;
with the proviso that $R^b$ is not 2-methylbenzothiazol-5-yl, 6-hydroxy-4-methyl-pyrimidin-2-yl, 3-carbomethoxypyrazin-2-yl, 5-carbomethoxypyrazin-2-yl, 4-carboethoxy-1-phenylpyrazol-5-yl, 3-methylpyrazol-5-yl, 4-chloro-2-methylthiopyrimidin-6-yl, 2-trifluoromethyl-1,3,4-thiadiazol-5-yl, 5,6,7,8-tetrahydro-2-naphthyl, 4-methylthiazol-2-yl, 6,7-dihydroindan-5-yl, 7-chloro-5-methyl-1,8-naphthyridin-2-yl, 5,7-dimethyl-1,8-naphthyridin-2-yl, or 3-cyanopyrazol-4-yl; and that if $R^b$ is 5-quinolyl or 4-pyridyl then $R^b$ is substituted by at least one substituent that is not hydrogen;
or a pharmaceutically acceptable salt of the compound.

2. The method of claim 1, wherein the compound is selected from the group consisting of:

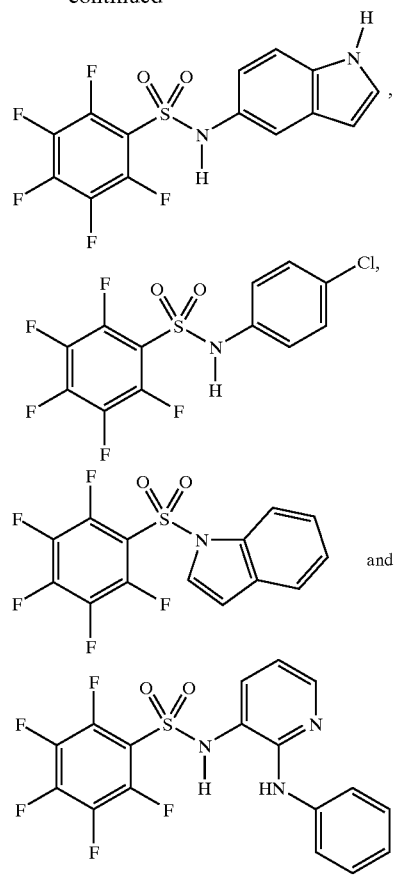

or a pharmaceutically acceptable salt thereof.

3. The method of claim 1, wherein the compound is

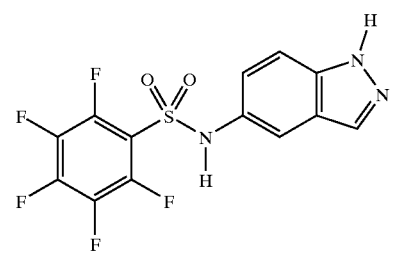

or a pharmaceutically acceptable salt thereof.

4. The method of claim 1, wherein Z is a substituent of the formula

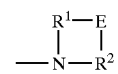

and the ring formed by N, $R^1$, E, $R^2$ contains 5 or 6 members.

5. The method of claim 1, wherein the compound is selected from the group consisting of:
4-Methyl-6-methoxy-2-pentafluorophenylsulfonamidopyrimidine;
4,6-Dimethoxy-2-pentafluorophenylsulfonamidopyrimidine;
2-Pentafluorophenylsulfonamidothiophene;

3-Pentafluorophenylsulfonamidothiophene;
3-Pentafluorophenylsulfonamidopyridine;
4-Pentafluorophenylsulfonamidopyridine;
1-Pentafluorophenylsulfonylindole;
1-Pentafluorophenylsulfonyl(2,3-dihydro)indole;
1-Pentafluorophenylsulfonyl(1,2-dihydro)quinoline;
1-Pentafluorophenylsulfonyl(1,2,3,4-tetrahydro) quinoline;
2-Chloro-5-pentafluorophenylsulfonamidopyridine;
5-Pentafluorophenylsulfonamidoindazole;
6-Pentafluorophenylsulfonamidoquinoline;
2,3-Dihydro-5-pentafluorophenylsulfonamidoindole;
5-Pentafluorophenylsulfonamidobenzo[a]thiophene;
5-Pentafluorophenylsulfonamidobenzo[a]furan; and
2-Anilino-3-pentafluorophenylsulfonamidopyridine,
or a pharmaceutically acceptable salt thereof.

6. The method of claim 1, wherein Z is a substituent of the formula —$NR^aR^b$ and $R^a$ is H and $R^b$ is monocyclic heteroaryl.

7. The method of claim 1, wherein Z is a substituent of the formula —$NR^aR^b$ and $R^a$ is H and $R^b$ is bicyclic heteroaryl.

8. The method of claim 1, wherein Z is a substituent of the formula —$NR^aR^b$ and $R^a$ is H and $R^b$ is selected from the group consisting of 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

9. The method of claim 1, comprising inhibiting the growth of a target cell in the subject by contacting the cell with an effective amount of the compound, thereby treating or preventing the cancer or the cancerous condition.

10. The method of claim 1, wherein the composition is administered orally.

11. The method of claim 1, wherein the composition is administered intravenously.

12. The method of claim 1, wherein the composition is administered intramuscularly.

13. The method of claim 1, further comprising administration of a therapeutically effective amount of an antineoproliferative, chemotherapeutic, or cytotoxic agent that is not represented by formula I.

14. The method of claim 1, wherein the compound is a prodrug.

15. The method of claim 1, wherein the compound is conjugated to a targeting molecule which preferentially directs the compound to a targeted cell.

16. The method of claim 13, wherein the antineoproliferative, chemotherapeutic, or cytotoxic agent is selected from the group consisting of cyclophosphamide, methotrexate, adriamycin, cisplatin, daunomycin, vincristine, vinblastine, vinarelbine, paclitaxel, docetaxel, tamoxifen, flutamide, and hydroxyurea.

17. The method of claim 1, wherein the subject is human.

18. The method of claim 17, wherein the cancer is selected from the group consisting of Kaposi's sarcoma, Wilms tumor, lymphoma, leukemia, myeloma, melanoma, breast cancer, ovarian cancer, and lung cancer.

19. The method of claim 1, wherein the cancer or cancerous condition is cancer.

20. The method of claim 19, wherein the subject is human.

* * * * *